US010273292B2

(12) United States Patent
El Habib et al.

(10) Patent No.: US 10,273,292 B2
(45) Date of Patent: Apr. 30, 2019

(54) NON-HIV VACCINE ANTIGEN FROM THE VAGINAL MICROBIOTA CAPABLE OF INDUCING A MUCOSAL NEUTRALIZING PROTECTIVE ANTIBODY RESPONSE AGAINST HIV INFECTION

(71) Applicant: B CELL DESIGN, Limoges (FR)

(72) Inventors: Raphaëlle Claude El Habib, Chaponost (FR); Régis Sodoyer, Saint Genis les Ollieres (FR); Armelle Cuvillier, Saint-Jouvent (FR); Christiane Moog, Ostwald (FR)

(73) Assignee: B Cell Design SAS, Limoges (FR)

( * ) Notice: Subject to any disclaimer, the term of this patent is extended or adjusted under 35 U.S.C. 154(b) by 0 days.

(21) Appl. No.: 15/117,300

(22) PCT Filed: Feb. 5, 2015

(86) PCT No.: PCT/IB2015/050870
§ 371 (c)(1),
(2) Date: Aug. 8, 2016

(87) PCT Pub. No.: WO2015/118473
PCT Pub. Date: Aug. 13, 2015

(65) Prior Publication Data
US 2016/0347828 A1 Dec. 1, 2016

(30) Foreign Application Priority Data
Feb. 10, 2014 (EP) .................................. 14305174

(51) Int. Cl.
A61K 39/00 (2006.01)
C07K 16/12 (2006.01)
(Continued)

(52) U.S. Cl.
CPC ...... *C07K 16/1253* (2013.01); *A61K 39/0241* (2013.01); *A61K 39/12* (2013.01); *A61K 39/40* (2013.01); *C07K 16/1063* (2013.01); *C12N 7/00* (2013.01); *A61K 2039/505* (2013.01); *A61K 2039/575* (2013.01); *A61K 2039/58* (2013.01); *C07K 2317/21* (2013.01);
(Continued)

(58) Field of Classification Search
None
See application file for complete search history.

(56) References Cited

FOREIGN PATENT DOCUMENTS

WO    WO 92/06199       *  4/1992   ............ C12N 15/35
WO    2012/066331 A1    5/2012

OTHER PUBLICATIONS

McGowin et al. Draft Genome Sequences of Four Axenic Mycoplasma genitalium Strains Isolated from Denmark, Japan, and Australia, J. Bacteriol. 2012; 194(21): 6010-6011.*
(Continued)

Primary Examiner — Janet L Andres
Assistant Examiner — Stuart W Snyder
(74) Attorney, Agent, or Firm — Morgan, Lewis & Bockius LLP

(57) ABSTRACT

A new non-HIV vaccine antigen from *Mycoplasma* sp. permease capable of inducing a mucosal neutralizing protective antibody response against HIV infection, a neutralizing antibody directed to said antigen, and a method for the identification of new antigens from the mucosal microbiota for the development of vaccines against pathogens.

Figure 1:
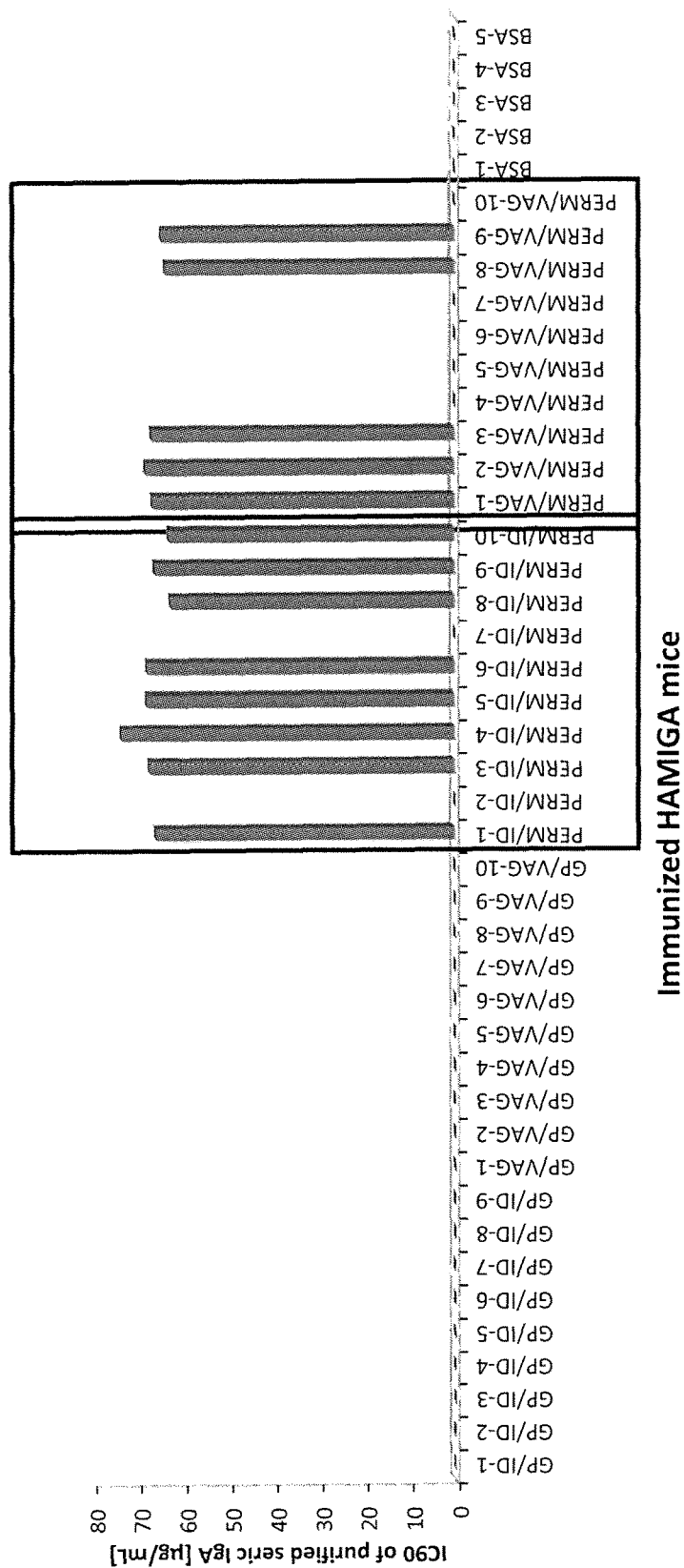
Figure 2:
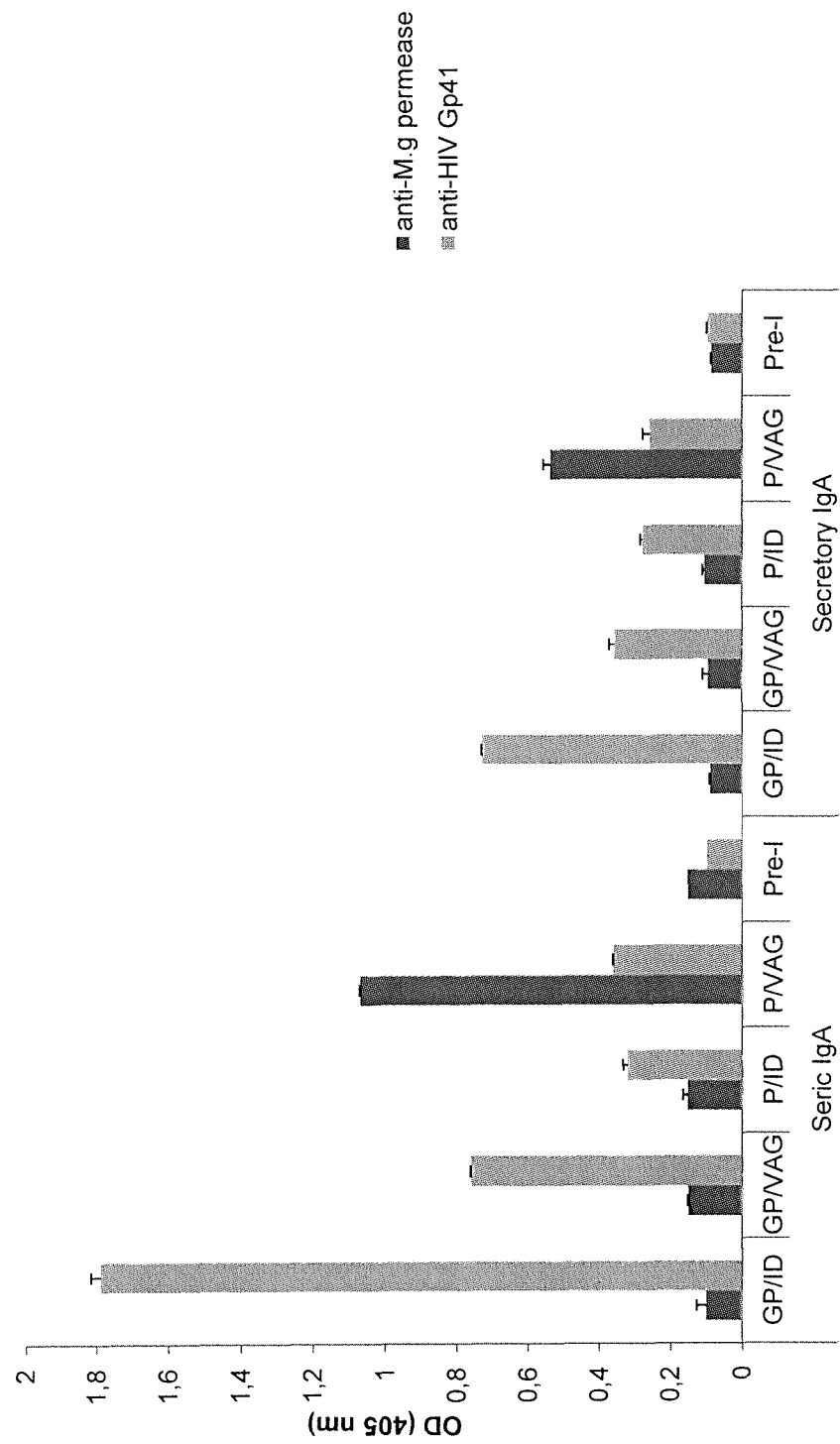
Figure 3:
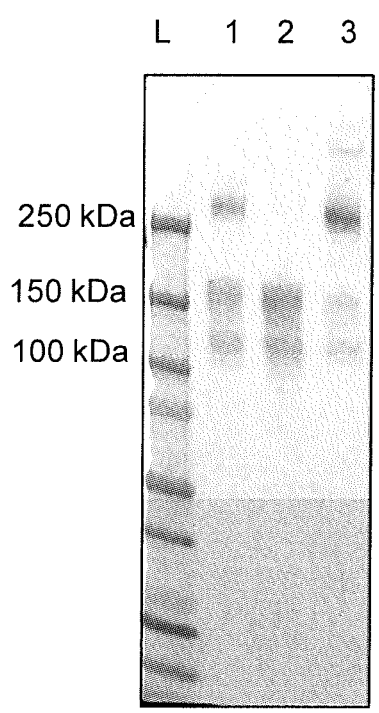
Figure 4:
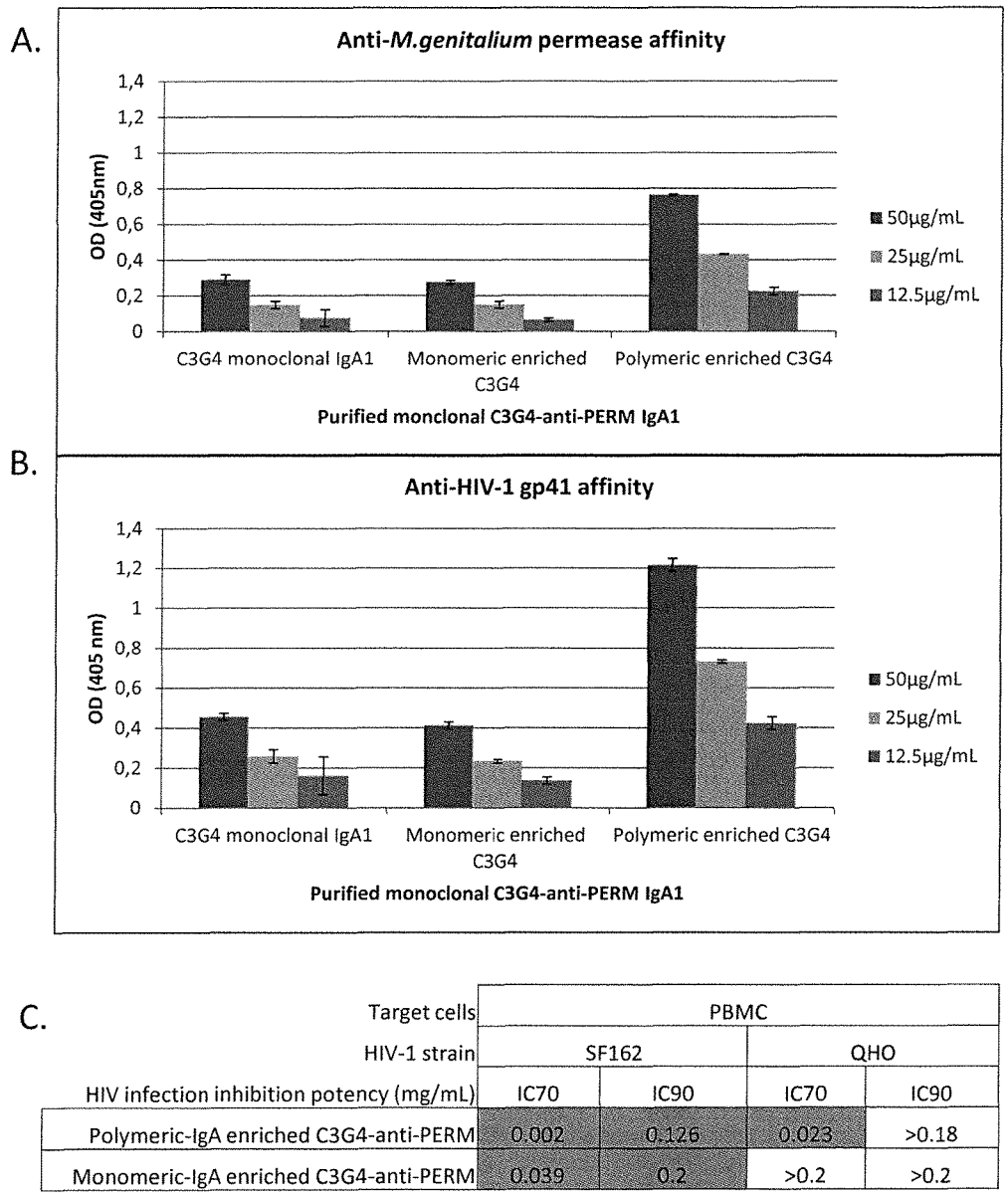

14 Claims, 6 Drawing Sheets
Specification includes a Sequence Listing.

(51) Int. Cl.
  *A61K 39/02*  (2006.01)
  *C07K 16/10*  (2006.01)
  *A61K 39/12*  (2006.01)
  *A61K 39/40*  (2006.01)
  *C12N 7/00*   (2006.01)

(52) U.S. Cl.
  CPC ...... *C07K 2317/24* (2013.01); *C07K 2317/33* (2013.01); *C07K 2317/52* (2013.01); *C07K 2317/55* (2013.01); *C07K 2317/56* (2013.01); *C07K 2317/76* (2013.01); *C12N 2740/16134* (2013.01)

(56) References Cited

OTHER PUBLICATIONS

GenBank AFQ04299.*
McElrath Selection of potent immunological adjuvants for vaccine construction. seminars in Cancer Biology, 1995; 6: pp. 375-385.*
Zhang and Baseman, Transcriptional response of Mycoplasma genitalium to osmotic stress. Microbiology. 2011; 157: 548-556.*
Machine translation of WO 92/06199 claims; downloaded from internet Sep. 11, 2017.*
International Search Report issued in corresponding International Patent Application No. PCT/IB2015/050870 dated Aug. 12, 2015.
Butt et al., "Mycoplasma genitalium: A comparative genomics study of metabolic pathways for the identification of drug and vaccine targets," Infection, Genetics and Evolution 12: 53-62 (2012).
Haggerty et al., "Mycoplasma genitalium: An Emerging Cause of Pelvic Inflammatory Disease," Infectious Diseases in Obstetrics and Gynecology (2011).
Fraser et al., "The Minimal Gene Complement of Mycoplasma genitalium," Science, 270: 397-403 (1995).
Vujanovic et al., "A Mycoplasma Peptide Elicits Heteroclitic CD4+ T Cell Responses against Tumor Antigen MAGE-A6," Clinical Cancer Research, 13: 6796-6806 (2007).
"RecName: Full=Uncharacterized ABC transporter permease MG468," XP002726236, EBI accession No. UNIPROT: Q49460, database accession No. Q49460 sequence.

* cited by examiner

```
VRC01     QVQLVQSGGQMKKPGESMRISCRASGYEFIDCTLNWIRLAPGKRPEWMGWLKPRGGAVNY  60
hVH1-2    QVQLVQSGAEVKKPGASVKVSCKASGYTFTGYYMHWVRQAPGQGLEWMGWINPNSGGTNY  60
C3G4      EVQMVESGGGLVKPGGSLKLSCAASGFAFNKYDMSWVRQTPAKRLEWVAYISGGGHTYY   60
mVH5-12   EVKLVESGGGLVQPGGSLKLSCAASGFTFSDYYMYWVRQTPEKRLEWVAYISNGGGSTYY  60
          :.*::* ..   * *:: :**:*:::******..*: : * .***: * :::..: . 4

VRC01     ARPLQGRVTMTRDVYSDTAFLELRSLTVDDTAVYFCTRGKNCDYNWDFEHWG-------  112
hVH1-2    AQKFQGRVTMTRDTSISTAYMELSRLRSDDTAVYYCAR----------------------  98
C3G4      RDTLKGRFTVSRDNAKNTLYLQMNSLKSEDTAMYYCTR-------HGTSWDYWGQGTALTVS  115
mVH5-12   PDTVKGRFTISRDNAKNTLYLQMSRLKSEDTAMYYCARGKNCDYNWDFEHWGRGTPVIVS  120
          . ::* **.: ** ..   *: : : .::.*** :*:*               5

VRC01    -         (SEQ ID NO: 17)
hVH1-2   -         (SEQ ID NO: 18)
C3G4     S 116     (SEQ ID NO: 19)
mVH5-12  S 121     (SEQ ID NO: 20)
```

FIGURE 6

NON-HIV VACCINE ANTIGEN FROM THE VAGINAL MICROBIOTA CAPABLE OF INDUCING A MUCOSAL NEUTRALIZING PROTECTIVE ANTIBODY RESPONSE AGAINST HIV INFECTION

SEQUENCE LISTING SUBMISSION VIA EFS-WEB

A computer readable text file, entitled "SequenceListing.txt" created on or about Jul. 20, 2016, with a file size of about 54 kb contains the sequence listing for this application and is hereby incorporated by reference in its entirety.

The invention relates to a new non-HIV vaccine antigen from the vaginal microbiota capable of inducing a mucosal neutralizing protective antibody response against HIV infection, to a neutralizing antibody directed to said antigen, and to a method for the identification of new antigens from the mucosal microbiota for the development of vaccines against pathogens.

Despite thirty years of study, there is no HIV vaccine. HIV-exposed uninfected individuals are currently the focus of intense studies because identifying the immune correlates of reduced susceptibility to HIV may offer important clues for the development of a HIV vaccine. It was hypothesized that hypermutated neutralizing monoclonal antibodies, isolated from HIV-infected patients, came from ancestor germinal B-cell lineages, primed initially by self- or non-HIV-1 antigens and boosted for HIV Env specific response by other immunogens (Haynes et al., Nature biotechnology, 2012, 30, 423-33). Along this line, it has been recently suggested to design HIV immunogens that target specific germline B-cell receptors (BCR; Jardine et al., Science, 2013, 340, 711-6). This was achieved by the "reverse-design" of antigens from the native HIV-gp120 CD4-binding site (CD4bs-gp120) epitope to initiate the binding with germline B-cells receptors. As expected, affinity comparison of various hypermutated neutralizing monoclonal antibodies (VRC01, 12A12, 3BNC60, NIH46-45 PGV04, PGV19, PGV20, VRC-CH31) with that of their germline version shows that the affinity of the antibody precursor is 2000 to 20000 times lower for the domain CD4bs-gp120 than that of the hypermutated versions (Hoot, S. et al., PLoS pathogens, 2013, 9, e1003106). Conversely, to determine the original epitope recognized by VRC01, several successive point mutations of CD4bs-gp120 domain were needed to better fit with the germinal BCR (composed by an heavy chain encoded by unmutated hVH1-2*2). According to the authors, only rare mutation events changing the antigenic nature of gp120 during infection would generate an epitope capable of activating a population of naive B-cells, precursors of a protective antibody response. This population would not be recruited by the native form of the envelope protein. The difficulty of this approach is to trace the historical evolution of viral antigens during the infection in the patient. In addition reverse-designed HIV antigens were not shown to be capable of eliciting HIV neutralizing antibodies by active immunisation.

The transgenic mouse strain HAMIGA (EP patent 1 680 449) is a humanized transgenic mouse strain expressing human/murine chimeric IgAs with human IgA heavy chain constant regions (CH1 to CH3) and mouse heavy chain variable region and light chain variable and constant regions (VH, VL and CL).

The inventors have shown that a monoclonal IgA antibody isolated from humanized HAMIGA transgenic mice immunised with a recombinant truncated permease of *Mycoplasma genitalium* (fragment 431 to 875 of *M. genitalium* ABC transporter permease protein GenBank accession number AAC72488.1 or SEQ ID NO: 1), a potential pathogen of the genital tract, is able to neutralize HIV-1 primary isolates. This is one of the rare HIV-1 neutralizing monoclonal antibody induced by active immunisation (Nishiyama, Y. et al., The Journal of Biological Chemistry, 2009, 284, 30627-30642; Sreepian, A. et al., Journal of Immune based Therapies and Vaccines, 2009, 7, 5) and the first to be elicited by a HIV-1 independent antigen. All the others have been isolated from HIV infected patients (McCoy, L. E. & Weiss, R. A. The Journal of Experimental Medicine, 2013, 210, 209-223). The characteristics of this IgA antibody and the nature of the immunogen suggest that the natural immune response to genital microbiota (commensals and/or pathogens) may contribute to the natural resistance to HIV infection.

In view of these results, *Mycoplasma genitalium* permease protein (SEQ ID NO: 1) and other *Mycoplasma* species. (M. sp.) permeases capable of inducing antibodies cross-reacting with *M. genitalium* permease protein of SEQ ID NO: 1 represent promising candidates to initiate an anti-HIV vaccine protocol based on their ability to prime B-cell clones, able to further recognize native HIV-antigens.

Therefore, a first aspect of the invention relates to a *Mycoplasma* sp. permease antigen or a polynucleotide encoding said antigen in expressible form for use as a medicament.

The antigen of the invention which is capable of inducing a specific immune response is for use as a vaccine, in particular an anti-HIV vaccine.

In the following description, unless otherwise specified, *Mycoplasma* permease, M. sp. permease, M. permease or permease refers to *M. genitalium* permease protein (SEQ ID NO: 1) and other *Mycoplasma* species. permeases capable of inducing antibodies cross-reacting with *M. genitalium* permease protein of SEQ ID NO: 1 *Mycoplasma genitalium* permease is the product of the locus tag MG 468 (complement of positions 570994 to 576345 on *Mycoplasma genitalium* G37 genome sequence GenBank accession number L43967.2). *M. genitalium* permease amino acid sequence corresponds to GenBank accession number AAC72488.1 or SEQ ID NO: 1.

In the following description, the standard one letter amino acid code is used.

The *Mycoplasma* sp. permease antigen or permease antigen according to the invention refers to an antigen comprising a protein/peptide derived from M. sp. permease, which protein/peptide is capable of inducing anti-permease antibodies which cross-react with HIV and neutralize HIV. The antibodies induced by the permease antigen which cross-react with HIV and neutralize HIV are named hereafter as anti-permease antibodies, HIV cross-reactive and neutralizing or HIV cross-reactive and neutralizing anti-permease antibodies.

In particular, the permease antigen of the invention is capable of priming B-cell clones able to further recognize native HIV-antigens.

The invention encompasses isolated antigens derived from M. sp. permease, isolated polynucleotides encoding said antigens, as well as the natural permease antigen of *Mycoplasma* sp. and the natural polynucleotide of *Mycoplasma* sp. encoding said antigen. The isolated permease antigens include isolated, natural, recombinant and synthetic antigens comprising or consisting of *Mycoplasma* sp. permease protein or immunogenic derivatives thereof such as for example M. sp. permease variants, peptide fragments of said protein or variants, and modified proteins/peptides derived from said protein, variants or fragments.

M. sp. permease protein variants are derived from wild-type amino acid sequences by the introduction of one or more mutations (deletion, insertion, and/or substitution) at specific amino acid positions. M. sp. permease protein variants include natural variants resulting from M. sp. permease gene polymorphism as well as artificial variants.

The antigens derived from M. sp. permease protein are functional antigens, which means that they are capable of inducing anti-permease antibodies, HIV cross-reactive and HIV infection neutralizing.

The HIV cross-reactive and neutralizing antibodies which are induced by the permease antigen of the invention recognize related epitopes in M. sp. permease and HIV Env proteins.

The permease antigen of the invention which is capable of inducing a broadly neutralizing protective immune response against HIV infection is useful as preventive and/or therapeutic HIV vaccine.

The properties of the permease protein/peptide antigen of the invention can be readily verified by technique known to those skilled in the art such as those described in the examples of the present application.

The polynucleotide encoding the antigen in expressible form refers to a nucleic acid molecule which, upon expression in a cell or a cell-free system results in a functional antigen. According to a preferred embodiment, said permease antigen comprises or consists of a *Mycoplasma*. sp. permease protein, a functional variant thereof or a functional fragment of at least 5 consecutive amino acids from said permease protein or variant. In some embodiments, the permease antigen derives from *M. genitalium* permease protein of SEQ ID NO: 1.

Preferably, said permease antigen comprises at least:

a) a protein comprising or consisting of an amino acid sequence sequence (I) which is at least 70% identical to SEQ ID NO: 4, preferably at least 75%, 80%, 85%, 90% or 95% identical to SEQ ID NO: 4, and b) a peptide of at least 5 consecutive amino acids from said protein in a), and wherein said protein in a) and peptide in b) are capable of inducing HIV cross-reactive and neutralizing anti-permease antibodies.

The amino acid sequence SEQ ID NO: 4 corresponds to a truncated permease protein (residues 431 to 875 of *M. genitalium* permease amino acid sequence SEQ ID NO: 1) including HIV cross-reactive neutralizing epitopes from the ectodomain and C-terminal tail of HIV gp41.

The permease antigen which is capable of inducing anti-permease antibodies which cross-react with HIV and neutralize HIV comprises at least one B cell or antibody epitope from M. sp. permease which is a HIV cross-reactive and neutralizing epitope.

The permease epitope cross-reacts preferably with an HIV-Env epitope, more preferably a HIV-gp41 epitope.

The permease epitope may advantageously cross-react with a HIV-gp41 ectodomain epitope from SEQ ID NO: 2.

Alternatively, the permease epitope may advantageously cross-react with an epitope of HIV-gp41 C-terminal tail. The permease epitope may cross-react with the amino acid sequence: LVGLRIVFAVLSIVNRVRQGYSPLSFQTH-LPTPRGP (SEQ ID NO: 3) from HIV-gp41 C-terminal tail (positions 699 to 734 of HIV gp41, according to the numbering system of Ratner et al., Nature, 1985, 313, 277-284), which exhibits sequence homology with M. sp. permease protein, in particular with *M. genitalium* permease of SEQ ID NO: 1, as demonstrated in the examples of the present application.

The permease antigen of the invention comprises one or more HIV cross-reactive and neutralizing epitope(s), wherein each epitope may be either linear or conformational. In some embodiments, the permease antigen comprises at least two identical or different HIV cross-reactive and neutralizing epitopes from M. sp. permease linked to each other directly or via a peptidic spacer arm.

The percent amino acid sequence identity is defined as the percent of amino acid residues in a Compared Sequence that are identical to the Reference Sequence after aligning the sequences and introducing gaps if necessary, to achieve the maximum sequence identity. The Percent identity is then determined according to the following formula: Percent identity=$100\times[1-(C/R)]$, wherein C is the number of differences between the Reference Sequence and the Compared sequence over the entire length of the Reference sequence, wherein (i) each amino acid in the Reference Sequence that does not have a corresponding aligned amino acid in the Compared Sequence, (ii) each gap in the Reference Sequence, and (iii) each aligned amino acid in the Reference Sequence that is different from an amino acid in the Compared Sequence constitutes a difference; and R is the number amino acids in the Reference Sequence over the length of the alignment with the Compared Sequence with any gap created in the Reference Sequence also being counted as an amino acid.

Alignment for purposes of determining percent amino acid sequence identity can be achieved in various ways known to a person of skill in the art, for instance using publicly available computer software such as BLAST (Altschul et al., J. Mol. Biol., 1990, 215, 403-). When using such software, the default parameters, e.g., for gap penalty and extension penalty, are preferably used. For amino acid sequences, the BLASTP program uses as default a word length (W) of 3 and an expectation (E) of 10.

The sequence (I) is preferably selected from the group consisting of SED ID NO: 4 and a sequence which differs from SEQ ID NO: 4 by dispersed deletions and/or insertions of one to five amino acids in said sequence, amino acid substitutions, and/or N-terminal deletion(s) of one or more amino acids in said sequence. The amino acid substitution(s) in SEQ ID NO:4 are advantageously chosen from conservative substitutions, i.e., substitutions of one amino acid with another which has similar chemical or physical properties (size, charge or polarity), which generally does not adversely affect the antigenic properties of the protein/peptide. More preferably, said conservative substitution(s) are chosen within one of the following five groups: Group 1-small aliphatic, non-polar or slightly polar residues (A, S, T, P, G); Group 2-polar, negatively charged residues and their amides (D, N, E, Q); Group 3-polar, positively charged residues (H, R, K); Group 4-large aliphatic, nonpolar residues (M, L, I, V, C); and Group 5-large, aromatic residues (F, Y, W).

The permease antigen of the invention may be a full length permease protein or an immunogenic fragment thereof. In some embodiments the permease antigen comprises or consists of a protein of less than 500 amino acids, preferably of less than 400, 300, 200, 100, 50, 40 or 30 amino acids.

Examples of preferred permease antigens comprise a protein comprising or consisting of SEQ ID NO: 4 or SEQ ID NO: 7.

The invention encompasses permease protein/peptide comprising or consisting of natural amino acids (20 gene-encoded amino acids in a L- and/or D-configuration) linked via a peptide bond as well as peptidomimetics of such protein where the amino acid(s) and/or peptide bond(s) have been replaced by functional analogues. Such functional analogues include all known amino acids other than said 20 gene-encoded amino acids. A non-limitative list of non-coded amino acids is provided in Table 1A of US 2008/0234183 which is incorporated herein by reference. The invention also encompasses modified proteins/peptides derived from the above proteins/peptides by introduction of any chemical modification into one or more amino acid residues, peptide bonds, N- and/or C-terminal ends of the protein/peptide, as long as the modified peptide/protein is functional. These modifications which are introduced into the protein/peptide by the conventional methods known to those skilled in the art, include, in a non-limiting manner: the substitution of a natural amino acid with a non-proteinogenic amino acid (D amino acid or amino acid analog); the modification of the peptide bond, in particular with a bond of the retro or retro-inverso type or a bond different from the peptide bond; the cyclization, and the addition of a chemical group to the side chain or the end(s) of the protein/peptide, in particular for coupling an agent of interest to the protein of the invention. These modifications may be used to increase its antigenicity, immunogenicity and/or bioavailability, or to label the protein/peptide. For example, the permease antigen may be conjugated to a GPI moiety for anchoring the antigen to the cell membrane and exposing said antigen at the cell-surface.

In another embodiment the permease antigen is a fusion or chimeric protein comprising an amino acid sequence fused to the N-terminal and/or C-terminal end(s) of a permease protein/peptide as defined above. The length of the chimeric protein is not critical to the invention as long as the permease antigen is functional. The permease protein/peptide is fused to one or more other protein/peptide moieties including other antigen(s), in particular HIV antigens, and/or other protein/peptide moieties which enhance B-cell activation, and/or trafficking to the lymph nodes, and/or increase the stability, bioavailability, and/or allow the purification, detection, immobilization, production in expression systems, of the permease antigen of the invention.

These moieties may be selected from: (i) a protein component of a virus-like particle for exposing the antigen of the invention at the surface of virus-like nanoparticles, (ii) a membrane anchoring moiety such as the transmembrane domain of a transmembrane protein for anchoring the antigen at the cell-surface and exposing said antigen at the cell-surface (iii) a labeling moiety such as a fluorescent protein (GFP and its derivatives, BFP and YFP), (iv) a reporter moiety such as an enzyme tag (luciferase, alkaline phosphatase, glutathione-S-transferase (GST), β-galactosidase), (v) a binding moiety such as an epitope tag (polyHis6, FLAG, HA, myc.), a DNA-binding domain, a hormone-binding domain, a poly-lysine tag for immobilization onto a support, (vi) a stabilization moiety, and (vii) a targeting moiety for addressing the chimeric protein to a specific cell type or cell compartment. In addition, the permease antigen may be separated from the peptide/protein moiety by a linker which is long enough to avoid inhibiting interactions between the permease antigen peptide and the protein/peptide moiety. The linker may also comprise a recognition site for a protease, for example, for removing affinity tags and stabilization moieties from the purified chimeric protein according to the present invention.

In some embodiments, the permease antigen consists of one permease-derived protein/peptide. In other embodiments, the permease antigen comprises several identical or different permease-derived proteins and/or peptides, directly or indirectly linked to each-other by covalent or non-covalent bounds.

The polynucleotide encoding the protein/peptide in expressible form is synthetic or recombinant DNA, RNA or combination thereof, either single- and/or double-stranded. Preferably the polynucleotide comprises a coding sequence which is optimized for the host in which the protein/peptide is expressed.

In another preferred embodiment, the polynucleotide comprises or consists of SEQ ID NO: 5 or 6.

In another preferred embodiment, the polynucleotide is inserted in a vector. Preferably, said recombinant vector is an expression vector capable of expressing said polynucleotide when transfected or transformed into a host cell such as a prokaryotic or eukaryotic cell. The polynucleotide is inserted into the expression vector in proper orientation and correct reading frame for expression. Preferably, the polynucleotide is operably linked to at least one transcriptional regulatory sequence and, optionally to at least one translational regulatory sequence. Recombinant vectors include usual vectors used in genetic engineering, vaccines and gene therapy including for example plasmids and viral vectors.

Another aspect of the present invention relates to an immunogenic or vaccine composition, comprising at least the permease antigen or the polynucleotide encoding said antigen, and a pharmaceutically acceptable vehicle, and optionally, at least one pharmaceutically acceptable carrier and/or adjuvant.

The immunogenic or vaccine composition according to the invention is capable of inducing a functional mucosal protective immune response against HIV infection which can be measured by various assays which are known to those skilled in the art. Examples of such assays include with no limitation: HIV virus capture assays, Antibody-Dependent-Cellular-Cytotoxicity (ADCC) assays using primary CD89+-polynuclear effector cells, Fc-mediated inhibition assays on macrophages, macrophage phagocytosis induction assays, viral replication inhibition assays, HIV infection neutralizing assays, virus aggregation assays and transcytosis inhibition assays.

In some embodiments, the pen lease antigen is an isolated antigen. In other embodiments the permease antigen comprises whole-cell live, attenuated or inactivated *Mycoplasma* sp. Preferably, the permease antigen comprises live, attenuated or inactivated *M. genitalium*.

The polynucleotide encoding said antigen is preferably inserted in an expression vector.

The composition comprises a therapeutically effective dose of the antigen/polynucleotide/vector, e.g., sufficient to induce a specific protective immune response against HIV, in the individual to whom it is administered. The effective dose is determined and adjusted depending on factors such as the composition used, the route of administration, the physical characteristics of the individual under consideration such as sex, age and weight, concurrent medication, and other factors, that those skilled in the medical arts will recognize.

The composition is generally administered according to known procedures used for vaccination, at dosages and for periods of time effective to induce a specific protective immune response against HIV. The administration may be by injection or by oral, sublingual, intranasal, rectal or vaginal administration, inhalation, or transdermal application. Preferably, the administration is by intradermal injection or intranasal, intravaginal or intrarectal administration.

The pharmaceutical vehicles are those appropriate to the planned route of administration, which are well known in the art.

The carrier may advantageously be selected from the group consisting of: uni- or multi-lamellar liposomes, ISCOMS, virosomes, viral pseudo-particles, saponin micelles, saccharid (poly(lactide-co-glycolide)) or gold microspheres, and nanoparticules. Preferably, the composition comprises liposomes.

The adjuvant may advantageously be selected from the group consisting of: polyI:C (polyinosine-polycytidylic acid), oil emulsion, mineral substances, bacterial extracts, CpG-containing oligonucleotide, saponin, alumina hydroxide, monophosphoryl-lipid A (MPLA, a TLR4 agonist) and squalene. Preferably, the adjuvant is capable of inducing an IgA antibody response, such as for example, polyI:C (polyinosine-polycytidylic acid) adjuvant. More preferred adjuvants include polyI:C and MPLA. The composition is formulated for administration by a number of routes. Preferably, the composition is formulated for intradermal injection or local application, more preferably for intradermal, intranasal, intravaginal, or intrarectal administration. For example, the composition is formulated in a gel for local application.

According to a preferred embodiment, said composition further comprises an antibody directed to said permease antigen; the antibody forms an antigen-antibody complex with the antigen which has the advantage of increasing the immunogenicity of the antigen. Preferably, the antibody is an IgA, more preferably a human or humanized IgA. The antibody is advantageously a monoclonal antibody. For example, the antibody is a human chimeric IgA, such as the human chimeric IgA monoclonal antibody C3G4 comprising a murine IgVH segment of SEQ ID NO: 8, a murine IgVL segment of SEQ ID NO: 9, a human Ig-alpha1 constant segment of SEQ ID NO: 10 and a murine Ig-kappa constant segment of SEQ ID NO: 11, which is disclosed in the examples of the present application.

A preferred vaccine composition comprises a *M. genitalium* permease antigen formulated in liposomes containing monophosphoryl lipid A (MPLA). Both liposomes and MPLA contribute as adjuvant. One mL of liposomal suspension may contain 1 mg of *M. genitalium* permease antigen and 0.800 mg of MPLA. The vaccine composition may be formulated as a gel, for local route administration, for example nasal or vaginal route. The gel may comprise 4% w/w Natrosol® 250 HHX (Hydroxyethyl cellulose) and 1.1% w/w Benzyl alcohol, in PBS.

Another aspect of the present invention relates to a permease antigen or a polynucleotide encoding said antigen as defined above, as a prophylactic and/or therapeutic vaccine, for use in the prevention and/or treatment of HIV infection.

The invention provides also a method of vaccination against HIV infection, comprising: administering to an individual a therapeutically effective amount of the permease antigen, polynucleotide and/or vector as described above, preferably included in an immunogenic or vaccine composition as described above.

The administration of the permease antigen is used to prime B-cell clones, able to further recognize native HIV-antigens. Following, the initial priming, the anti-HIV immune response may be boosted by administration of HIV antigen(s), in particular HIV-Env antigen(s). A mixture of different HIV antigens may be used. Preferred HIV antigens are HIV gp41 ectodomain and/or C-terminal tail antigens.

The vaccination protocol may comprise an initial priming with the permease antigen comprising three administrations of permease antigen at one month interval and a final boost with HIV-1 antigen(s), one month after the last administration of permease antigen.

Another aspect of the invention relates to a combined preparation containing a permease antigen, polynucleotide, vector as described herein and HIV antigen(s), in particular HIV-Env antigen(s), for the simultaneous, separate or sequential use in the prevention and/or treatment of HIV infection.

In a preferred embodiment, said HIV infection is HIV-1 infection.

Another aspect of the invention relates to an isolated anti-permease antibody which is HIV cross-reactive and neutralizing, or a functional fragment of said antibody comprising at least the antibody binding site. Preferably, the antibody is an IgA, more preferably a human or humanized IgA, such as a human chimeric IgA. The antibody is advantageously a monoclonal antibody. In a preferred embodiment, the antibody is human chimeric IgA monoclonal antibody produced by immunisation of an HAMIGA transgenic mouse (EP patent 1 680 449) with a permease antigen as described above. For example, the antibody is the human chimeric IgA monoclonal antibody C3G4 comprising a murine IgVH segment of SEQ ID NO: 8, a murine IgVL segment of SEQ ID NO: 9, a human Ig-alpha1 constant segment of SEQ ID NO: 10 and a murine Ig-kappa constant segment of SEQ ID NO: 11, which is disclosed in the examples of the present application.

Another aspect of the invention relates to an isolated polynucleotide encoding said HIV cross-reactive and neutralizing anti-permease antibody or functional fragment thereof. In a preferred embodiment, the polynucleotide comprises the sequence SEQ ID NO: 12 or 13 which encodes the IgVH segment of SEQ ID NO: 8 and the IgVL segment of SEQ ID NO: 9, respectively.

The anti-permease antibody is a useful component of the immunogenic or vaccine composition as described above, it is also a companion diagnostic tool to evaluate the protective immune status evolution and maturation of patients treated or immunized against HIV infection, a predictive marker of resistance to HIV infection and a tool for designing HIV immunogens capable of inducing a protective neutralizing antibody response against HIV infection.

Further aspect of the present invention concerns a method for the identification of a new vaccine candidate antigen against a pathogen of interest, comprising:

a) identifying an antigen in the mucosal microbiota of an individual naturally resistant to said pathogen, preferably a human individual, wherein the microbiotal antigen is from a microorganism different from said pathogen, b) generating an antibody against said microbiotal antigen in a), c) assaying the neutralizing activity of the antibody obtained in b) against said pathogen, wherein a neutralizing activity of the antibody against said pathogen indicates that the microbiotal antigen is a new vaccine candidate antigen against said pathogen, for an individual which is susceptible to said pathogen.

The natural microbiota may be from the vaginal, nasopharyngeal, lung or gastro-intestinal mucosa.

The pathogen is a microorganism which may be pathogenic in some individuals but not pathogenic in other individuals which differ from the first ones by some factors such as for example age, sex, medical history, immune status and microbiota.

According to a preferred embodiment, the pathogen is a virus.

In some embodiments of said method, said pathogen is HIV and/or said microbiota is from the vaginal mucosa. The antibody is advantageously generated by immunization of an HAMIGA transgenic mouse (EP patent 1 680 449) with the microbiotal antigen, to produce human chimeric IgAs directed against said antigen.

A neutralizing activity is indicative that the microbiotal antigen is capable of inducing a protective immune response against said pathogen. The neutralization activity may be related to an antibody which recognizes epitopes which may not be identified by standard binding assays.

Another aspect of the invention is a M. sp. permease antigen derived from *M. genitalium* as defined above, said permease antigen being different from M. sp. protein. Preferably, said M. sp. permease antigen is a *M. genitalium* permease antigen, more preferably SEQ ID NO: 4 or 7. The invention encompasses also a modified protein/peptide and a chimeric protein derived from said M. sp. permease antigen, preferably from a *M. genitalium* permease antigen. The invention further includes a polynucleotide encoding said M. sp. permease antigen, preferably a *M. genitalium* permease antigen, in particular the polynucleotide of SEQ ID NO: 5 or 6, and a vector comprising said polynucleotide.

The polynucleotide for use according to the invention is prepared by the conventional methods known in the art. For example, it is produced by amplification of a nucleic sequence by PCR or RT-PCR, by screening genomic DNA libraries by hybridization with a homologous probe, or else by total or partial chemical synthesis. The recombinant vectors are constructed and introduced into host cells by the conventional recombinant DNA and genetic engineering techniques, which are known in the art.

The protein/peptide for use according to the invention is prepared by the conventional techniques known to those skilled in the art, in particular by expression of a recombinant DNA in a suitable cell system (eukaryotic or prokaryotic) or by solid-phase or liquid-phase synthesis. More specifically, the protein and its derivatives are usually produced from the corresponding cDNA, obtained by any means known to those skilled in the art; the cDNA is cloned into an eukaryotic or prokaryotic expression vector and the protein produced in the cells modified with the recombinant vector is purified by any suitable means, in particular by affinity chromatography. The peptide and its derivatives are usually solid-phase synthesized, according to the Fmoc technique, originally described by Merrifield et al. (J. Am. Chem. Soc., 1964, 85: 2149-) and purified by reverse-phase high performance liquid chromatography.

The practice of the present invention will employ, unless otherwise indicated, conventional techniques which are within the skill of the art. Such techniques are explained fully in the literature. In addition to the above arrangements, the invention also comprises other arrangements, which will emerge from the description which follows, which refers to exemplary embodiments of the subject of the present invention, with reference to the attached drawings in which:

FIG. 1 illustrates HIV-1 infection neutralization potency (IC90) in PBMC-based neutralizing assay of purified seric IgA from HAMIGA mice immunized with *Mycoplasma genitalium* permease antigen (PERM) or HIV gp41-ectodomain polypeptide (GP). HAMIGA mice (10 mice per group) were immunized via two different routes (vaginal route (VAG) or intradermal route (ID)) and with two different antigens, a recombinant truncated permease antigen from *M. genitalium* (PERM) or the HIV gp41-ectodomain polypeptide (GP). Control HAMIGA mice (5 mice per group) were immunized with Bovine Serum Albumin (BSA) by the ID route. Seric IgA were collected and purified by affinity chromatography. Neutralizing activity of seric IgA from each immunized mouse was measured against SF162 virus strain in a PBMC based-neutralizing assay. The neutralizing activity is expressed as IC90 (Inhibitory concentration 90%), i.e., the concentration (μg/mL) of purified seric IgA that caused a 90% reduction of HIV virus infection. Only seric IgAs from permease immunized mice were able to exhibit an IC90 potency of HIV-1 infection neutralization at the range of 60 μg/mL. Despite a strong anti-gp41 binding, none of the seric IgAs from gp41-ectodomain polypeptide immunized mice was able to generate an IC90 neutralizing immune response.

FIG. 2 shows cross-reactivity by ELISA of anti-*Mycoplasma genitalium* permease polyclonal seric and secretory IgA antibodies with HIV gp41. HAMIGA transgenic mice were immunized with *Mycoplasma genitalium* (M.g.) permease antigen (P) or gp41-ectodomain polypeptide (GP) by the intradermal (ID) or intra-vaginal (VAG) routes. Anti HIV-1 gp41 and anti-M.g. permease specific polyclonal IgA antibodies were analysed by ELISA in serum and vaginal secretions of Pre-immune mice (Pre-I) and immunized mice. Although polyclonal IgA (seric and vaginal) from gp41-immunized HAMIGA mice do not show a significant binding on the permease in ELISA, polyclonal IgA from *M. genitalium* permease-immunized HAMIGA mice exhibit a significant cross-reactivity against gp41 ectodomain antigen.

FIG. 3 represents Coomassie-blue-stained SDS-PAGE analysis of HIV-1 neutralizing human/murine chimeric monoclonal $IgA1_{\kappa}$ antibody C3G4. C3G4 was purified by affinity-chromatography and monomeric and polymeric forms of IgA were separated by size-exclusion chromatography. C3G4 contains the two forms—monomeric and polymeric—of a monoclonal IgA1. L: molecular weight marker. 1. Total fraction of mAb C3G4. 2. Monomeric-IgA enriched fraction of mAb C3G4. 3. Polymeric-IgA enriched fraction of mAb C3G4.

FIG. 4 illustrates the binding and neutralizing activity of C3G4 monoclonal anti-*M. genitalium* permease IgA1. A. The binding of total IgA, monomeric IgA-enriched and polymeric IgA-enriched fractions of C3G4 to *M. genitalium* permease was analysed by ELISA using truncated *M. genitalium* permease as antigen. B. The binding of total IgA, monomeric IgA-enriched and polymeric IgA-enriched fractions of C3G4 to HIV gp41 was analysed by ELISA using HIV gp41-ectodomain polypeptide as antigen. C. Neutralizing activity of monomeric IgA and polymeric IgA enriched fractions of C3G4 was measured against HIV-1/SF162 and HIV-1/QHO virus strains in a PBMC based-neutralizing assay. The neutralizing activity is expressed as IC70 (Inhibitory concentration 70%) and IC90 (Inhibitory concentration 90%), i.e., the concentration (mg/mL) of monomeric enriched or polymeric enriched fraction of C3G4 that caused a 70% and 90% reduction of HIV virus infection, respectively.

FIG. 5 illustrates the neutralization activity of C3G4 monoclonal anti-*M. genitalium* permease IgA1 in PBMC-based neutralizing assay on nine HIV-1 strains. Neutralizing activity of purified C3G4 polymeric IgA1 was tested on different HIV-1 laboratory and primary strains. Purified C3G4 polymeric IgA1 exhibited a neutralization activity on nine different HIV-1 strains with an IC80<18 μg/mL against HIV-1$_{SF162}$, HIV-1$_{92BR025}$ and HIV-1$_{TV1}$ isolates, an IC50<1.8 μg/mL against HIV-1$_{QHO}$ and HIV-1$_{DU174}$ isolates and an IC50<18 μg/mL against HIV-1K$_{ON}$, HIV-1$_{92UG024}$, HIV-1$_{89.6}$ and HIV-1$_{RW}$ isolates.

FIG. 6 represents the alignment of IgH variable segments of HIV neutralizing human mAb VRC01 (SEQ ID NO: 17) directed to CD4bs-gp120 and its human unmutated ancestor IgVH1-2*2 (SEQ ID NO: 18); HIV-1 neutralizing human/murine chimeric monoclonal IgA1$_κ$ antibody C3G4 (SEQ ID NO: 19) and its murine unmutated ancestor IgVH5-12 (SEQ ID NO: 20).

EXAMPLE 1: IDENTIFICATION OF THE VAGINAL IMMUNE RESPONSE IN UNINFECTED WOMEN HIGHLY EXPOSED TO HIV

1. Material and Methods
1.1 Cohorts

A cohort of 32 HIV highly-exposed uninfected women (HEUW) from sero-discordant couples was investigated in collaboration with the GHESKIO Centers (Haitian Group for the Study of Kaposi's Sarcoma and Opportunistic Infections) in Haiti. The control cohort included 15 HIV non-exposed uninfected subjects. None of the subjects had CCR5-Delta 32 homozygous genotype and two were heterozygous, one in HEUW group, the other in control group. The study was approved by ethical committee and informed consent was obtained from all women prior sampling.

1.2 ELISA on Vaginal Secretions

Vaginal secretions of HEUW and controls were assayed for HIV gp41-specific IgG1 and IgA antibody responses by ELISA, as previously described (Hocini et al., AIDS Res. Hum. Retroviruses, 1997, 13, 1179-).

1.3 Western-Blot on Vaginal Secretions

Vaginal secretions of HEUW and controls were assayed for HIV gp160, gp110, gp41, p68, p55, p53, p40, p34 and p25 specific IgG1 and IgA antibodies by Western-Blot as previously described (Hocini et al., AIDS Res. Hum. Retroviruses, 1997, 13, 1179-).

1.4 Inhibition of Transcytosis Assay

Inhibition of transcytosis of assay was performed as previously described (Bélec, L. et al. The Journal of infectious diseases, 2001, 184, 1412-1422).

1.5 Cloning of Mucosal Cells IgG1 and IgA Variable Regions into Phagemid Vector

Separate libraries of IgA and IgG1 Fab fragments were constructed. Briefly, messenger RNAs extracted from mucosal cells of two selected subjects were used for separate amplification of IgG1 and IgA variable regions. PCR primers corresponding to the 5' end of all VH and VL variable domain families were combined individually with a primer derived from IgG1 or IgA first constant domain (Persson et al., Proc. Natl. Acad. Sci. USA., 1991, 88, 2432-6). The amplified DNA fragments corresponding to heavy and light chains were then cloned into a phagemid vector (Persson et al., Proc. Natl. Acad. Sci. USA., 1991, 88, 2432-6), allowing the surface display of Fab fragment (Barbas et al., Proc. Natl. Acad. Sci. USA, 1991, 88, 7978-82).

1.6 Sequencing of Recombinant IgG and IgA Fab

Individual clones, from both IgG1 and IgA libraries were sequenced using the standard Sanger dideoxy technique.

1.7 Expression of Recombinant IgG1 and IgA Fab Fragments

Recombinant Fab fragments were expressed using both *E. coli* (Studier and Moffat, J. Mol. Biol., 1986, 189, 113-130) and Cell-free translation (Ryabova et al., Methods Mol. Biol. 1998, 77, 179-93).

1.8 Analysis of VH Mutations

VH mutations of recombinant IgG1 and IgA were analysed as described in Wang et al., BMC bioinformatics, 2008, 9 Suppl 12, S20.

1.9 Identification of Antibody Epitope by Phage Displayed Random Peptide Libraries Screening In order to identify the epitope recognized by the antibody, the recombinant antibody Fab fragment was screened against commercial phage displayed random peptide libraries (Ph.D.-12™ Phage Display Peptide Library Kit, NEW ENGLAND BIOLABS), according to the manufacturer's instructions. Typically, 4 to 5 rounds of selection (biopanning) were applied.

1.10 Statistical Analysis

A Yates' chi-squared test was used to analyze the samples from Table I. The difference between control group and HIV-highly exposed group is statistically significant as long asp value<0.05.

2. Results

The immune response in the genital tract of a cohort of HIV highly exposed uninfected women (HEUW) from sero-discordant couples was investigated in collaboration with the GHESKIO Centers (Haitian Group for the Study of Kaposi's Sarcoma and Opportunistic Infections) in Haiti. Vaginal fluids from 32 individuals were analyzed by ELISA and Western Blot, and compared with 15 control HIV non-exposed uninfected subjects. None of the subjects had CCR5-Delta 32 homozygous genotype and two were heterozygous, one in HEUW group, the other in control group. Vaginal secretions were tested for specific IgG1 and IgA antibody responses against gp41 in ELISA. ELISA results were confirmed by western blot. Only samples showing a strong positivity with both techniques were retained for further investigation and antibody library construction.

Although all subjects were seronegative for HIV infection, 53% of the HEUW were positive in vaginal secretions for anti-gp41 IgA versus only 13% in the control group (p<0.02) whereas no significant difference was observed for anti-gp41 IgG responses (Table I).

TABLE I

HIV-1 specific immune response in vaginal secretions of HEUW by WB and ELISA

| Antibody | Positives in Control group (n = 15) | Positives in HIV highly exposed group (n = 32) | P value |
| --- | --- | --- | --- |
| IgA WB/gp160 | 0 (0%) | 3 (10%) | NS |
| IgA WB/gp110 | 0 (0%) | 1 (3%) | NS |
| IgA WB/p68 | 0 (0%) | 1 (3%) | NS |
| IgA WB/p55 | 0 (0%) | 2 (6%) | NS |
| IgA WB/p53 | 0 (0%) | 1 (3%) | NS |
| IgA WB/gp41 | 2 (13%) | 17 (53%) | 0.02 |
| IgA WB/p40 | 0 (0%) | 1 (3%) | NS |
| IgA WB/p34 | 0 (0%) | 4 (12%) | NS |
| IgA WBP/p25 | 1 (6%) | 2 (6%) | NS |
| IgA ELISA/gp41 | 3 (20%) | 9 (28%) | NS |
| IgG1 WB/gp160 | 0 | 5 (16%) | 0.16 |
| IgG1 WB/gp110 | 0 | 2 (6%) | NS |
| IgG1 WB/p68 | 0 | 1 (3%) | NS |
| IgG1 WB/p55 | 2 (13%) | 3 (10%) | NS |
| IgG1 WB/p53 | 0 | 4 (12%) | NS |
| IgG1 WB/gp41 | 2 | 8 (25%) | NS |
| IgG1 WB/p40 | 0 | 2 (6%) | NS |
| IgG1 WB/p34 | 0 | 1 (3%) | NS |

TABLE I-continued

HIV-1 specific immune response in vaginal
secretions of HEUW by WB and ELISA

| Antibody | Positives in Control group (n = 15) | Positives in HIV highly exposed group (n = 32) | P value |
|---|---|---|---|
| IgG1 WB/p25 | 0 | 4 (12%) | NS |
| IgG1 ELISA gp41 | 2 (13%) | 7 (22%) | NS |

WB: Western blot;
NS: non-significant

The functional activity of the secretions was tested by inhibition of transcytosis of $HIV_{JRCSF}$. None of the secretions were positive in transcytosis functional assays, compared with the broad HIV-1 neutralizing monoclonal antibody 2F5 used as positive control. Therefore the transcytosis test was not further used for screening of samples.

To characterize the antibody response, mucosal cells were collected with a cytobrush from two CCR5 wild type subjects selected on the basis of their strong response against gp41 in ELISA and Western Blot and of long term unprotected sexual relationship with at least one HIV-1 seropositive partner. In order to avoid amplifying genes from the partner, all samples positive for the Prostate Specific Antigen (>50 ng/mL PSA) were discarded.

After specific amplification, IgG and IgA variable regions were cloned into a phagemid vector allowing the expression of Fab fragments at the surface of filamentous phages. In a first strategy, phages displaying a Fab binding to a recombinant gp41 antigen would have been selected. This screening step was found to be unnecessary due to the observed strongly oligoclonal profile of the cloned repertoire. In a standard situation, the analysis by sequencing of clones randomly picked from the library should give a whole set of different sequences. However, in the case of the selected subjects, the vast majority of clones was identical or very closely similar and represented a large percentage of the total population (up to 75% for VH chains). This was not due to a bias in amplification or cloning since the same result was obtained when independent libraries were constructed. The same was true for both the IgG1 and IgA libraries. To further characterize this oligoclonal mucosal repertoire, Fab fragments corresponding to the most represented antibodies were expressed as recombinant proteins.

IgG1 (called Toussaint) in association with 2 different light chains, IgA (called Makandal) in association with 2 different light chains, IgG1 (Jacmel) and IgA (Mangue). The most represented light chains were from κ1 and λ4 families. These two light chains were systematically associated with all the heavy chains since the original VH/VL chain pairing was not possible to determine. Analysis of the VH mutations showed that Makandal had a germinal un-mutated profile. In order to identify the recognized epitope, this antibody was screened against commercial phage displayed random peptide libraries. In two independent screenings, two overlapping peptides allowed for the identification of an epitope corresponding to a region in the C-terminal part of gp41: LVGLRIVFAVLSIVNRVRQGYSPLSFQTHLPTPRGP (SEQ ID NO: 3).

It was hypothesized that the mucosal oligoclonal immune response of these women might be responsible for their resistance to HIV infection and that these antibodies were induced in response to a particular microbiota and by cross-reaction with the gp41 domain of HIV envelope, could prevent the viral fusion. In order to see if the sequence of amino acids recognized by Makandal Fab had any homologies with other proteins of the environment, this sequence was compared with a protein sequence databases excluding HIV proteins. Data showed very weak matches, but interestingly, there were consistent matches with bacterial protein sequences. Among these, a permease from *Mycoplasma genitalium* (GenBank accession number AAC72488.1 or SEQ ID NO: 1) was selected.

EXAMPLE 2: THE PERMEASE ANTIGEN OF *M. GENITALIUM* IS CAPABLE OF INDUCING A SYSTEMIC AND A MUCOSAL NEUTRALIZING PROTECTIVE ANTIBODY RESPONSE AGAINST HIV INFECTION IN HAMIGA MICE

1. Material and Methods
1.1 Antigens
Recombinant Truncated Permease from *M. Genitalium* (rPermease or PERM)

Recombinant truncated permease cDNA (SEQ ID NO: 6) prepared by gene synthesis (GeneART) was inserted in a procaryotic expression vector (pSP401, derived from pET28 cer (NOVAGEN); Peubez et al., Microbial Cell factories, 2010, 9, 65-) and expressed in *E. coli* BL21 strain. Tagged by a Histidine tail, the antigen (SEQ ID NO: 7) was purified by affinity chromatography on His-IMAC (BIORAD) column. The purified recombinant permease protein fragment ([rPermease]=1 mg/mL in Tris 25 mM, Arginine 0.5 M, Sucrose 5% buffer, pH 8) had a purity of 82%.

HIV Gp41 Ectodomain Peptide (GP)

Recombinant HIV-gp41 ectodomain peptide (GP) preparation is disclosed in Krell et al., European Journal of Biochemistry, 2004, 271, 1566-1579. Briefly, a 0.6 kb DNA fragment containing the sequence encoding the ectodomain of gp41 of HIV isolate LAI (amino acid sequence SEQ ID NO: 2, corresponding to amino acid residues 540 to 673 of gp160 (SEQ ID NO: 14)), was obtained by PCR amplification using, as template, a plasmid containing the gp120 sequence and the gp41 sequence of the LAI isolate. The start codon in the forward primer is a naturally occurring methionine residue. A stop codon and the DNA sequence encoding the extension GGGGSHHHHHH (SEQ ID NO: 15) were added to the reverse primer. Platinum HF polymerase (GIBCO INVITROGEN) was used, according to the manufacturer's instructions, for PCR amplification. The PCR amplified fragment was cloned directly into the vector pM1800 using the restriction sites NcoI and XhoI. The expression vector pM1800 is a derivate of pET28c (NOVAGEN, in which the F1 origin of replication has been deleted and replaced with the Cer fragment, allowing for multimer resolution. For protein expression, *E. coli* BL21(DE3) was transformed with the corresponding plasmids. Tagged by an Histidine tail, the ectodomain antigen (SEQ ID NO: 16) was purified by affinity chromatography on onto a 5 ml Hi-Trap Chelating column (AMERSHAM PHARMACIA BIOTECH). Protein elution was achieved using a buffer comprising 50 mMTris/HCl, 8 M urea, 500 mM NaCl and 500 mM imidazole, pH 8.0. Protein refolding was achieved by dialysis with 50 mM formate, pH 2.8. Protein was then sterile filtered and stored at −45° C.

1.2 Immunization

Immunization was performed in HAMIGA transgenic mice (EP Patent 1 680 449), a transgenic mouse strain producing human/mouse chimeric IgAs with human IgA heavy chain constant regions and mouse light chain constant regions and (heavy and light chain) variable regions. Estrous cycles of HAMIGA transgenic mice were synchronized by treatment with Depoprovera (5 days before the first immunization, 8 days- and 16 days post-immunization-2 mg/mouse/injection by subcutaneous route). HAMIGA transgenic mice (10 mice per group) were immunized by intradermal (Group ID in ear) or intravaginal (Group VAG) routes twice at two weeks of interval with the recombinant truncated permease of M. genitalium (PERM) in polyI:C adjuvant (10 µg/mouse/injection, ratio 1:2.5 PolyI:C (25 µg/mouse/injection, INVIVOGEN)). For comparison, ten HAMIGA mice were immunized with gp41-ectodomain polypeptide via the ID route (GP/ID, 10 µg/mouse/injection, in polyI:C adjuvant (10 µg/mouse/administration, ratio 1:2.5 PolyIC (25 µg/mouse/injection, INVIVOGEN)) and via the vaginal route (GP/VAG, 10 µg/mouse/administration, in polyI:C adjuvant (10 µg/mouse/administration, ratio 1:2.5 PolyIC (25 µg/mouse/administration, INVIVOGEN)). As a negative control, five HAMIGA mice were immunized with Bovine Serum Albumin (BSA) antigen by ID route.

1.3 Vaginal Washes Harvest

Vaginal cavities of immunized mice were washed each day during a complete estrous cycle (4 days), by gently flushing vaginal cavity with 200 µL of physiological media (NaCl 0.9%, URGO).

1.4 Seric IgA and Secretory IgA Concentration Titration by ELISA

Seric IgA from immunized HAMIGA mice (purified by affinity chromatography) and secretory IgA prepared from vaginal washes were titered by ELISA. Briefly, 96-well plates (Maxisorp®, NUNC) were coated with 1 µg/mL of goat anti-human IgA (BECKMAN COULTER) in PBS buffer overnight at 4° C. Plates were saturated with a BSA 2%/PBS1× buffer during 30 minutes at 37° C. Incubation of the samples (secretory IgA, diluted 10 times in BSA 0.2%/PBS or purified seric IgA, diluted 100 times in BSA 0.2%/PBS) was performed at 37° C. during 2 h. Human IgA reference range (from [control hIgA]=0.2 mg/ml to 1.56 ng/mL) was incubated following the same protocol and revealed by an Alkaline-Phosphatase (AP) labelled-goat anti-hIgA polyclonal antibody (BECKMAN COULTER; diluted 2000 times in BSA 0.2%/BSA).

1.5 Preparation of Monoclonal IgA

To isolate monoclonal IgA from permease-immunised mice, immortalization of specific B-cell lymphocytes were performed, according to Kölher and Milstein protocol (Köhler, G. & Milstein, C. European Journal of Immunology, 1976, 6, 511-9). Briefly, splenocytes from permease-immunized mice were fused with mice myeloma cells (X63 Sp2/0) and subcloned on 96-wells plates. The supernatants of hybridoma clones were harvested after three weeks of culture and tested for their neutralizing activity on in vitro HIV infection inhibition assay. Each clone was cryopreserved in DMSO 10%/SVF 20%/DMEM media in liquid nitrogen.

1.6 IgA Purcation

IgA were purified by affinity chromatography. The monomeric and polymeric forms of IgA were separated by size exclusion column chromatography.

1.7 Antigen Specificity Analysis

Permease fragment/gp41-ectodomain specific IgA were assessed by ELISA using Maxisorp® 96-wells plates (NUNC) coated with 1 to 5 µg/mL of antigens overnight at 4° C. Crude supernatants, unpurified IgA from vaginal washes or purified serum IgA (diluted in PBS/Gelatin 0.2%) were incubated 2 hours at 37° C. Specific IgA binding was revealed with an AP-conjugated goat anti-human IgA antibody (1/2000 diluted, BECKMAN COULTER).

1.8 Cell Preparation

Blood samples were collected from anonymous healthy donors (Etablissement Français du Sang, EFS). Peripheral Blood Mononuclear cells were obtained by Ficoll-Hypaque sedimentation of Buffy coats. PBMCs were activated with phytohemagglutinin-A (PHA, 1 mg/mL, SIGMA) in RPMI medium-10% fetal calf serum (FCS) supplemented with antibiotics (Penicillin and Streptomycin, 100 Units/mL and 100 µg/mL, respectively) at the concentration of $10.10^6$ cells/mL for 30 minutes. Cells were then cultivated in RPMI medium-10% FCS supplemented with antibiotics at $2.10^6$ cells/mL. After 3 days, cells were frozen. PBMCs from 5 donors were thawed, pooled and culture for one day before being used in the neutralization assay.

TZM-B1 cell line was obtained through the NIH reagent program. TZM-B1 cells were cultured in RPMI medium-10% FCS supplemented with antibiotics (Penicillin and Streptomycin, 100 Units/mL and 100 µg/mL, respectively).

1.9. Virus Preparation

Primary HIV-1 isolates were amplified on human blood leukocytes, as described previously (Holl et al., Blood, 2006, 107, 4466-4474). Virus stocks collected at peak virus production were concentrated 70-fold with a 100-kDa cutoff polyethersulfone filter (Centricon® Plus-70 Biomax Filter; MILLIPORE). Primary HIV-1 isolates were obtained from the National Institute for Biological Standards and Control (NIBSC): HIV-$1_{SF162}$ isolate (subtype B, R5), HIV-$1_{QH0}$ isolate (subtype B, R5 strain, R5), HIV-$1_{89.6}$ (sub-type B, X4R5), Viruses HIV-$1_{DU174}$ (subtype C, R5), HIV-$1_{92BR025}$ (subtype C R5), HIV-$1_{92UG024}$ (subtype D, X4), HIV-$1_{KON}$ (subtype CRF02-AG, X4). HIV-1 BaL (subtype B) was provided by S. Gartner, M. Popovic, and R. Gallo (NIH).

Pseudoviruses HIV-$1_{SF162}$ and HIV-$1_{QH0}$ (SF162.LS and QH0692.42) were produced by co-transfection of 293T cell line with EnvC3 back bone and Envs from HIV-$1_{SF162}$ and HIV-$1_{QH0}$ respectively.

1.10 Neutralization Assays

Neutralization assays were performed on human PBMC and TZM-bl cells, as previously described (Mascola et al., J. Virol., 2005, 79, 10103-10107), using two standard reference strains of clade B as Env-pseudotypes viruses (SF162.LS and QH0692.42; Li et al., J. Virol., 2005, 79, 10108-10125). The 50%, 70%, 80% or 90% inhibitory dose was defined as the sample concentration that caused 50%, 70%, 80% or 90% reduction in relative luminescence units (RLU; Li et al., J. Virol., 2005, 79, 10108-10125) in TZM-bl or percentage of infected cells in PBMC, respectively.

1.11 Fc-Mediated Inhibition of HIV Replication in MDMs

Fc-mediated inhibition assay was performed on Monocyte derived macrophages (MDMs). MDMs were generated by culture of CD14+ monocytes with GM-CSF for 5 days. Inhibition of cell free HIV-1 SF162 or HIV-1 BaL replication in MDMs was assessed as previously described by Holl et al. (J. Virol., 2006, 80, 6177-6181; J. Immunol., 2004, 173, 6274-6283). Briefly, antibodies and virus were incubated for 1 h before addition to MDMs. Virus replication was measured after 48 h by the intracellular staining of p24 in MDMs by flow cytometry. Percentage of infected cells compared to control infected macrophages without antibodies was determined.

2. Results

A truncated permease antigen from *M. genitalium* (SEQ ID NO: 7, corresponding to amino acid sequence 431-875 of *M. genitalium* permease sequence SEQ ID NO: 1) was expressed in *E. coli* and used to immunize HAMIGA transgenic mice expressing chimeric human IgA. Groups of ten HAMIGA mice received two administrations of permease fragment in Poly I-C adjuvant via the intradermal (Group PERM/ID) and vaginal routes (Group PERM/VAG). At the same time, groups of ten HAMIGA mice were immunized with gp41-ectodomain polypeptide (SEQ ID NO: 16) (Group GP/ID; Group GP/VAG). As a negative control, five HAMIGA mice were immunized with BSA antigen (Group BSA) by ID route. IgA from vaginal washes and purified serum IgA from immunized and control HAMIGA mice were analysed.

To identify the immunization route and the antigen able to induce neutralizing immune response, neutralizing activity of seric IgA from each immunized mouse was measured against SF162 virus strain, a tier 1 isolate, in a PBMC-based neutralizing assay (FIG. 1). Although all seric IgA of PERM-immunized mice show ability to cross-react with HIV gp41 epitopes in ELISA (FIG. 2), only eight seric IgA from PERM/ID immunized mice and five seric IgA from PERM/VAG immunized mice were able to exhibit a strong potency of HIV-1 infection neutralization with an IC90 in a range of 60 μg/mL (FIG. 1). Despite a strong anti-gp41 binding (FIG. 2), no seric IgA from GP/ID and GP/VAG immunized mice groups was able to reach IC90 neutralizing activity (FIG. 1). As expected, in Bovine Serum Albumin (BSA)-immunized mice group, purified seric IgAs showed no gp41 binding by ELISA nor HIV-1 infection neutralization activity (FIG. 1).

In addition, only vaginal IgA pools from PERM/ID and PERM/VAG immunized group (n=10) exhibited a strong neutralization activity against HIV-$1_{SF162}$ (a tier 1 isolate,) with the lowest IC90 (in a range of 1.5 to 2.5 μg/mL; Table II). Vaginal IgA pools from PERM/VAG immunized group (n=10) reached an IC50<2.5 μg/mL against QHO isolate (a tier 2 isolate) when performed in a TZM-bl cells based infection inhibition assay.

TABLE II

HIV-1 specific neutralizing activity of purified vaginal IgA pools from immunized HAMIGA mice

| Group of immunized | | Target cells: PBMC | | Target cells: TZM | |
|---|---|---|---|---|---|
| | | Percentage of inhibition of HIV-1 infection | | | |
| | | IC90 | | IC50 | |
| | | HIV-1 virus | | | |
| HAMIGA (n = 10) | | SF162 | QHO | SF162 | QHO |
| Vaginal IgA | GP/ID | 0.010 | >0.010 | >0.01 | >0.01 |
| Vaginal IgA | GP/VAG | >0.016 | >0.016 | 0.016 | 0.016 |
| Vaginal IgA | PERM/ID | 0.0015 | >0.0015 | >0.0015 | >0.0015 |
| Vaginal IgA | PERM/VAG | 0.0025 | >0.0025 | 0.002 | 0.0025 |
| Vaginal IgA | Pre-immune | >0.0035 | >0.0035 | >0.0035 | >0.0035 |
| Vaginal IgA | BSA | 0.0115 | >0.0115 | >0.0115 | >0.0115 |

*HIV-Infection Inhibition titers are expressed in mg/mL

The supernatants of hybridoma clones from permease-immunised mice were tested for neutralizing activity in a PBMC assay against the HIV-$1_{SF162}$ isolate. Out of 900 hybridoma supernatants, 141 showed 80% neutralisation of the viral infection including 34 that showed 90% neutralization potency. One clone, C3G4, was sub-cloned three times and anti-permease specificities were confirmed by ELISA. One clone named C3-G4.EA5.IH2.JA11 was finally stabilized. The variable segments of the neutralizing immunoglobulin, a human chimeric IgA$1_{,\kappa}$, were sequenced and analysed on IMGT data base (www.imgt.org/vquest).

The supernatant of C3G4 contains both a monomeric and polymeric monoclonal IgA1 (FIG. 3, line 1). Fractions enriched in monomeric (FIG. 3, line 2) and polymeric forms of IgA (FIG. 3, line 3) were prepared and their affinity for *M. genitalium* permease (FIG. 4, A) and cross-reactivity with HIV gp41 were tested in ELISA (FIG. 4, B). In each ELISA test, polymeric-IgA enriched form of C3G4 exhibited the highest affinity for *M. genitalium* truncated permease and gp41-ectodomain polypeptide.

Monomeric IgA and polymeric IgA enriched fractions of purified C3G4 were primarily tested in a PBMC neutralizing assay with two HIV-1 virus isolates, SF162 and QHO (FIG. 4C). Polymeric IgA enriched form strongly inhibited infec-

TABLE III

Sequence and analysis of the variable segments of the HIV-1 neutralizing human chimeric monoclonal IgA$1_{,K}$, C3G4

| Heavy chain | IgH-V | IgH-D | IgH-J |
|---|---|---|---|
| mab hIgA1 (C3G4 clone) | 5-12-1*01F | 1-1*01 | 2*01 F |
| Mouse germline gene Identity | 93.06% | | 82.98% |
| AA IgHV sequence | EVQMVESGGGLVKPGGSLKLSCAASGFAFNKYDMSVVVRQTPAK RLEVVVAYISGGGGHTYYRDTLKGRFTVSRDNAKNTLYLQMNSLKS EDTAMYYCTRHGTSWDYWGQGT (SEQ ID NO: 8) | | |

| Light chain | IgH-V | IgH-J |
|---|---|---|
| mab hIgA1 (C3G4 clone) | 15-103*01 | 1*01 F |
| Mouse germline gene Identity | 95.34% | 94.74% |
| AA IgLV sequence | DIQMNQSPSSLSASLGDTISITCRASQNINFWLSVVYQLKPGNIPKQ LIYKTSNLHTGVPSRFSGSGSGTDFTLTISSLQPEDIATYYCLQGQS YPWTFGGGTKLEIK (SEQ ID NO: 9) | | tion by both HIV-1 isolates SF162 (IC70 of 2 µg/mL) and QHO (IC70 of 23 µg/mL). 90% inhibition of HIV-1$_{SF162}$ isolate infection was achieved with 126 µg/mL of polymeric IgA enriched C3G4. In each test, polymeric form of C3G4 IgA showed a greater neutralizing potency than the monomeric IgA enriched form of C3 G4.

Monomeric and polymeric forms of C3G4 were also tested in a macrophage-based neutralization assay. The assay shows the Fc-mediated inhibitory activity of the antibodies. As shown in Table IV, both forms presented 80% inhibition potency in PBMC and Macrophages-based assays, in presence of 6 µg/mL and 14 µg/mL of C3G4 IgA, respectively. Ninety percent inhibition of HIV-1 infection was achieved when both tests were performed with 58 µg/mL of C3G4 IgA polymeric form. Polymeric form of C3G4 IgA showed a greater neutralizing potency than monomeric form. The higher avidity of polymeric form may allow the antibody to recognize and capture several viral particles, as opposed to the monomeric form.

TABLE IV

HIV-1 specific neutralizing activity of monomeric or polymeric enriched fractions of C3G4 IgA antibody

| | | Human cell type | | | |
|---|---|---|---|---|---|
| | | PBMC | | Macrophages | |
| | | HIV-1 isolate | | | |
| | | SF162 | | BaL | |
| | | HIV-1 infection inhibition titer (in mg/mL) | | | |
| | | IC80 | IC90 | IC80 | IC90 |
| Samples | C3G4-purified IgA1 (containing two forms mix) | >0.125 | >0.125 | 0.031 | 0.200 |
| | C3G4-enriched monomeric IgA1 | 0.094 | >0.094 | 0.023 | 0.094 |
| | C3G4-enriched polymeric IgA1 | 0.006 | 0.058 | 0.014 | 0.058 |

Figure 5:
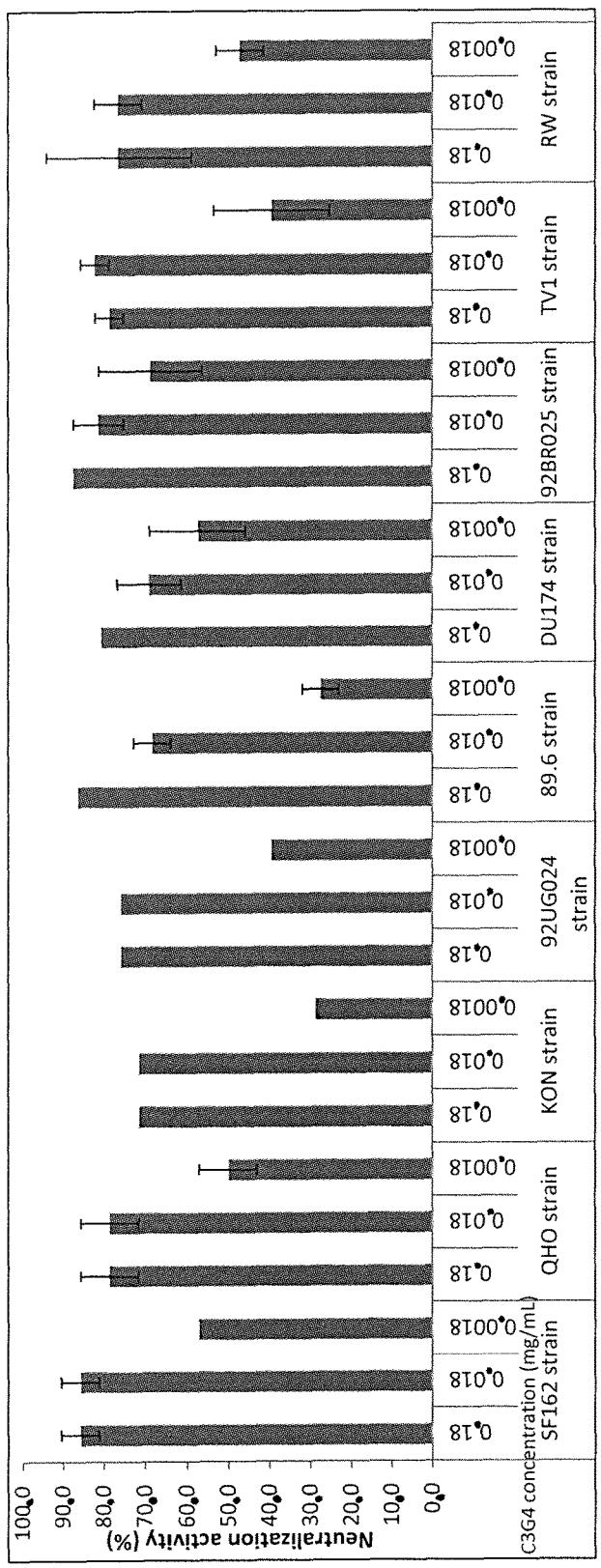

Neutralizing activity of monoclonal C3G4 IgA1 was also tested on different primary HIV-1 isolates (FIG. 5). Purified polymeric IgA1 exhibited a neutralization activity on nine different HIV-1 primary isolates at a low IC50 and IC80. C3G4 neutralized HIV-1$_{SF162}$, HIV-1$_{BR025}$ and HIV-1$_{TV1}$ isolates with a great potency (IC80 comprised in the range of 2 to 20 µg/mL). C3G4 neutralized HIV-1$_{QHO, KON, 92UG024, 89.6}$ and $_{RW}$ with moderate potency (IC80>20 µg/mL).

These data demonstrate that *Mycoplasma genitalium* permease antigen represents a HIV-1 vaccine candidate able to prime a mucosal and systemic broadly-neutralizing protective antibody response against HIV infection in the immunized individuals.

Discussion

In this study, using HAMIGA mice to produce IgA, immunization with *M. genitalium* permease adjuvanted with polyI:C administered via the ID or vaginal routes elicited specific IgA Abs able to recognize the HIV-Gp41 and to neutralize HIV-1 primary isolates.

IgA is the most abundant antibody isotype produced weekly and delivered by secretion in mucosal area. Because HIV infection is usually initiated at mucosal site of entrance, the inventors assumed that IgA would better mimic the response in mucosa, including the genital mucosa. Pivotal role of polymeric form of IgA is to prevent pathogen entry by immune exclusion, but also polymeric IgA are assumed to agglutinate the virus and block transcytosis (Chomont, N. et al. *Virology,* 2008, 370, 246-254) and with more efficacy than their IgG homologue (Hur, E. M. et al. *Blood,* 2012, 120, 4571-82).

The integrity of the mucosal immune system appears to be critical for the rate of the HIV infection progression, because it is severely compromised during acute HIV infection. Beside the massive depletion of CD4+T cells, the frequency of IgA-producing B-cells in mucosal area drops dramatically, decreasing luminal secretory IgA concentrations involved in pathogens-immune exclusion protective pathway (described in both HIV and SIV infection; Alam et al., J. Viral., 2008, 82, 115-125; Muro-Cacho et al., J. Immunol., 1995, 154, 5555-5566; Douek et al., 2006, Nat. Immunol., 2006, 7, 235-239).

Transgenic mice expressing human chimeric IgA (EP patent 1 680 449) were used to ensure selection of a monoclonal IgA class antibody since a conventional immunization of wild type mice usually conduct to an IgG specific response. This mouse line was modified to express a constant human IgA heavy chain whereas constant light chain and variable genes remain from mouse origin. The C3G4-neutralizing antibody was induced by active immunization where the murine and not human repertoire has been involved in the antigen recognition. The possibility to generate the same response in human can only be evaluated in clinical trials.

Resistance to HIV infection is a rare phenomenon. Although several mechanisms may contribute including genetic factors (CCR5 d32 mutation, MHC allotype.) or immune factors such as specific IgA in vaginal secretions directed against the HIV-1 gp41, other factors may be involved.

The human and murine Ab response to many common pathogens is oligoclonal, with a restricted usage of Ig V-genes (Bos, N. A. et al., Infection and Immunity, 1996, 64, 616-623; Baxendale, H. E. & Goldblatt, D., Infection and Immunity 2006, 74, 1025-1031). In addition, in the mucosa exposed to a multitude of germs, these Abs are polyreactive and establish a natural immune homeostasis (Shimoda et al., Immunology, 1999, 97, 9-17).

Therefore, the inventors propose that the innate response to the genital tract microbiota (commensals or pathogens) could also play a role against HIV (or other pathogens) infection. The innate characteristic of the response is suggested by the oligoclonal profile of IgA found in the HEUW and the germinal feature of the Ab. The isolation of an Ab against *M. genitalium* cross-reacting with gp41 and neutralizing HIV-1 provides additional evidence. Whereas current thinking is that vaccine should induce hypermutated Ab in order to neutralize HIV-1 (Klein, F. et al., Cell, 2013, 153, 126-38), the inventors propose that in mucosal site, main portal of entry of the virus, non affinity matured Ab elicited by specific commensals or pathogen, could neutralize and protect against HIV infection. HEUW may have a particular unique flora with native immune response that contributes to resistance to HIV-1 infection. Comparison of the microbiota in HEUW and women who later becomes infected will help to clarify this assumption.

The key for an effective vaccine strategy seems to be the identification of the priming antigen which elicits ancestor B lineage selection and proliferation for a future maturation all along its immune history. For some viral infections, the antigen that initially activates certain naive B-cell lineages and that stimulates the memory B-cells may not be identical.

The inventors propose that this population of naive B precursors may be recruited and primed by antigens, not only from past infections but from current natural commensal micro-organisms colonization. Immunization by *Mycoplasma genitalium* antigens induced cross-reactive anti-HIV antibodies and elicited a systemic and mucosal broadly neutralizing anti-HIV response. IgH variable segment of one of the neutralizing monoclonal antibodies from the present study reveals a highest homology with the murine germline ancestor IgVH5-12 (FIG. 6). Interestingly, this particular murine segment shows a strong identity with the human unmutated IgVH1-2*2, ancestor of VRC01 broadly HIV neutralizing monoclonal antibody (bNab). Comparison of the IgVH regions highlights a conserved sequence covering 50 of the 98 amino acid residues, including five canonical HIV-contact residues, and particularly $Arg^{71}_{C3G4-CRC01}$, which mimics the key interaction of $Arg^{59}_{CD4}$ and $Asp^{368}_{gp120}$ (Scheid, J. F. et al., Science, 2011, 333, 1633-1637). Even if all critical residues are not conserved, the comparison of IgVH5-12 with the human IgVH1-2*2 (S18 and S19, Jardine and Schief, Science, may 2013, vol 340) suggested that the close conformational architecture of the two ancestors may be the key point of their ability to further neutralize HIV-1 infection, hIgVH1-2*2 targeting the gp120 whereas mIgVH5-12 targeting the gp41 on the surface of HIV-1 viral particles.

The inventors propose *M. genitalium* permease as a promising candidate to initiate a vaccine protocol mainly at the mucosal level based on its ability to prime naive B-cell clones, able to further recognize native HIV-antigens.

The invention claimed is:

1. A method of inducing expression of a HIV-1 cross-reactive and HIV-1 neutralizing antibody in a human subject, comprising administering to the human subject an immunogenic composition comprising:
   (i) A *Mycoplasma genitalium* permease antigen comprising an amino acid sequence which is at least 85% identical to SEQ ID NO: 4 or a peptide of at least 5 consecutive amino acids thereof, or
   (ii) a polynucleotide encoding said antigen in expressible form,
   in an amount effective to induce expression of an HIV-1 cross-reactive, HIV-1 neutralizing, and anti-*Mycoplasma genitalium* permease antibody in the human subject, and a pharmaceutically acceptable adjuvant.

2. The method according to claim 1, wherein said permease antigen comprises the protein of SEQ ID NO: 4.

3. The method according to claim 1, wherein said permease antigen comprises the protein of SEQ ID NO: 7.

4. The method according to claim 1, wherein said polynucleotide comprises SEQ ID NO: 5.

5. The method according to claim 1, wherein said polynucleotide comprises SEQ ID NO: 6.

6. The method according to claim 1, wherein the HIV-1 cross-reactive and HIV-1 neutralizing antibody binds to HIV-1 gp41.

7. A method of inducing expression of an HIV-1 cross-reactive and HIV-1 neutralizing antibody in a human subject, comprising administering to the human subject a vaccine composition comprising:
   (i) a *Mycoplasma genitalium* permease antigen comprising an amino acid sequence which is at least 85% identical to SEQ ID NO: 4 or a peptide of at least 5 consecutive amino acids thereof, or
   (ii) a polynucleotide encoding said antigen in expressible form,
   in an amount effective to induce expression of an HIV-1 cross-reactive, HIV-1 neutralizing, and anti-*Mycoplasma genitalium* permease antibody in the human subject, and a pharmaceutically acceptable adjuvant.

8. The method according to claim 7, wherein said permease antigen comprises a permease epitope cross-reacting with an HIV-1 gp41 ectodomain or C-terminal tail epitope.

9. The method according to claim 8, wherein said permease epitope cross-reacts with an HIV-gp41 ectodomain epitope from SEQ ID NO: 2.

10. The method according to claim 7, wherein said permease antigen comprises the protein of SEQ ID NO: 4.

11. The method according to claim 7, wherein said permease antigen comprises the protein of SEQ ID NO: 7.

12. The method according to claim 7, wherein said polynucleotide comprises SEQ ID NO: 5.

13. The method according to claim 7, wherein said polynucleotide comprises SEQ ID NO: 6.

14. The method according to claim 7, wherein the HIV-1 cross-reactive and HIV-1 neutralizing antibody binds to HIV-1 gp41.

* * * * *

SEQUENCE LISTING

<160> NUMBER OF SEQ ID NOS: 20

<210> SEQ ID NO 1
<211> LENGTH: 1783
<212> TYPE: PRT
<213> ORGANISM: Mycoplasma genitalium

<400> SEQUENCE: 1

```
Met Phe Ser Phe Phe Lys Gln Ile Phe Lys Ser Leu Lys Lys Phe Phe
1               5                   10                  15

Phe Leu Leu Phe Gly Ile Ile Phe Val Leu Phe Ser Ile Ile Phe Leu
            20                  25                  30

Glu Thr Ser Ile Val Gln Leu Ser Asn Asn Leu Val Ser Thr Tyr Thr
        35                  40                  45

Thr Leu Val Ser Lys Thr Asn Ser Ser Asp Ile Val Ala Pro Ala Ile
    50                  55                  60

Leu Lys Glu Ala Asn Pro Val Tyr Ile Ala Ser Leu Thr Asn Asp Ser
65                  70                  75                  80

Gly Tyr Phe Ser Lys Ile Lys Ile Asp Asp Lys Lys Ile Asn Tyr Leu
                85                  90                  95

Phe Pro Tyr Gln Glu Asn Asp Phe Gly Ser Asp Ser Gly Gln Ser Asn
            100                 105                 110

Gly Ser Gly Asp Asn Gln Asn Lys Thr Ile Pro Arg Lys Gly Asp Val
        115                 120                 125

Asn Glu Lys Asp Lys Leu Phe Leu Ala Arg Lys Arg Gly Ile Leu Lys
    130                 135                 140

Ala Tyr Gly Glu Ala Asn Ile Ala Glu Lys Arg Ile Tyr Lys Gly Leu
145                 150                 155                 160

Ala Val Ser Phe Asn Asn Thr Asp Ser Phe Asn Gly Ser Asp Ile Ser
                165                 170                 175

Asp Ser Ile Thr Asn Arg His Ile Ile Ser Asp Pro Gln Asn Leu Ile
            180                 185                 190

Tyr Asp Ala Ser Gly Asn Leu Leu Gly Tyr Phe Ala Asp Gly Leu Ile
        195                 200                 205

Lys Glu Thr Ile Ser Leu Arg Ala Gly Ile Ala Arg Phe Pro Gly Asp
    210                 215                 220

Lys Gly Lys Ser Thr Gly Thr Gln Val Lys Ile Thr Gln Lys Gln Gln
225                 230                 235                 240

Thr Asn Asn Asp Pro Gln Lys Asp Ser Thr Val Asn Ser Leu Tyr Lys
                245                 250                 255

Thr Asn Asn Lys Asp Lys Val Trp Phe Lys Ser Asp Glu Thr Lys Ala
            260                 265                 270
```

```
Asp Asn Thr Asp Ile Ser Ala Asn Tyr Leu Phe Thr Gly Gly Asn Glu
            275                 280                 285
Ala Ala Asn Trp Phe Pro Asn Leu Tyr Ala Asn Ile Pro Ile Asp Leu
290                 295                 300
Glu Ile Asp Pro Gly Ser Gln Phe Trp Lys Asp Val Asn Pro Phe Lys
305                 310                 315                 320
Glu Ile Val Glu Phe Gln Thr Gln Lys Glu Ser Lys Asp Asn Gln
                325                 330                 335
Ser Phe Thr Leu Thr Phe Asn Leu Asp Ile Ser Lys Leu Asn Lys Leu
            340                 345                 350
Asp Asn Glu Gln Leu Lys Trp Leu Thr Asn Ala Lys Thr Ile Ala
            355                 360                 365
Asn Asn Ser Ser Phe Gly Asp Trp Asp Leu Glu Asn Lys Leu Lys Gln
370                 375                 380
Leu Lys Lys Phe Glu Leu Lys Ile Asn Lys Asp Trp Leu Lys Lys
385                 390                 395                 400
Val Glu Ser Glu Lys Asp Thr Ile Leu Asn Ser Leu Pro Gly Phe Ser
                405                 410                 415
Asp Ser Asp Lys Asp Thr Ile Phe Lys Thr Gln Asn Gly Met Met Val
                420                 425                 430
Arg Asn Asn Asn Leu Ser Phe Gln Pro Ser Ser Asn Asn Leu Gln Leu
            435                 440                 445
Val Gln Asn Gln Asn Ser Gln Ala Ser Asn Gly Ile Ala Asp Pro Asn
            450                 455                 460
Phe Ser Asn Val Gln Thr Ala Tyr Asn Lys Ile His Gln Ser Asn Asn
465                 470                 475                 480
Thr Pro Glu Lys Thr Leu Asp Ala Val Tyr Ala Ala Val Leu Asp Gln
            485                 490                 495
Trp Arg Ser Ile Phe Gln Glu Asp Leu Val Lys Lys Thr Val Asp Leu
            500                 505                 510
Leu Glu Lys Tyr Arg Asp His Phe Leu Lys Ala Thr Ala Phe Asn Asn
            515                 520                 525
Ile Asp Tyr Ser Lys Gln Asn Ile Ala Ile Ala Asn Asn Val Ser Ser
530                 535                 540
Ala Glu Ser Ala Ser Phe Leu Val Ser Asn Lys Asp Glu Gln Arg Tyr
545                 550                 555                 560
Asn Asp Leu Ser Leu Ile Asp Gly Val Asp Leu Lys Ser Trp Leu Phe
                565                 570                 575
Lys Pro Glu Gln Asn Glu Ser Asn Pro Leu Asp Thr Ile Tyr Gly Gly
            580                 585                 590
Gln Asp Ala Asn Asn Gly Phe Leu Gln Lys Ile Asp Tyr Glu Phe Lys
            595                 600                 605
Pro Ser Thr Ser Ser Gly Gly Met Thr Ala Ser Leu Lys Asn Thr Gln
            610                 615                 620
Ala Leu Ser Pro Lys Ser Thr Lys Phe Pro Ile Tyr Pro Lys Leu Ala
625                 630                 635                 640
Asn Ile Ile Ala Gln Ala Gln Leu Pro Glu Ala Thr Asn Ile Pro Thr
                645                 650                 655
Thr Ala Leu Asp Ala Leu Lys Gln Trp Thr Asn Leu Asp Ala Asn Gly
                660                 665                 670
Phe Asn Asn Leu Lys Glu Glu Asp Lys Arg Lys Ala Ala Asn Asn Tyr
            675                 680                 685
Leu Ala Leu Leu Ser Tyr Phe Thr Pro Ala Phe Gln Asp Pro Asn Glu
```

-continued

```
            690                 695                 700
Leu Ile Glu Thr Asn Arg Gln Met Leu Glu Ile Pro Ile Thr Val Lys
705                 710                 715                 720

Asn Gly Val Asn Pro Leu Ile Leu Pro Thr Asp Gln Gln Asn Leu Val
                725                 730                 735

Val Gln Thr Pro Glu Ala His Gly Ala Val Val Ser Gln Gln Trp Leu
                740                 745                 750

Phe Arg His Asn Lys Glu Ile Leu Pro Gln Glu Gly Tyr Ala Trp
                755                 760                 765

Lys Thr Ala Leu Gln Thr Pro Asn Asn Phe Pro Asn Trp Leu Asn Asp
770                 775                 780

Leu Pro Asp Arg Tyr Lys Phe Ser Ile Asn Gly Leu Thr Phe Ala Ile
785                 790                 795                 800

Leu Gly Ile Gly Glu Ser Val Glu Thr Gly Tyr Pro Val Leu Ser Leu
                805                 810                 815

Gln Ser Pro Leu Pro Asn Thr Gln Asp Glu Ala Leu Ile Phe Val Asn
                820                 825                 830

Asp Gln Ala Tyr Arg Ser Ile Leu Phe Ala Val Pro Ala Ala Asn Gln
                835                 840                 845

Glu Asn Tyr Tyr Ala Phe Lys Ser Thr Asp Leu Lys Gln His Thr Asp
850                 855                 860

Gln Asp Pro Val Gln Phe Ile Ala Asn Arg Leu Glu Gly Tyr Leu Asp
865                 870                 875                 880

Val Pro Arg Ser Asp Leu Ala Phe Asn Val Lys Asp Ile Ser Lys Phe
                885                 890                 895

Asn Tyr Leu Thr Thr Ala Arg Asn Tyr Phe Pro Asp Leu Val Gln Ser
                900                 905                 910

Tyr Leu Ala Ile Val Ser Thr Val Ile Ala Ile Phe Leu Ile Ile Leu
                915                 920                 925

Ala Leu Tyr Leu Ile Ile Leu Leu Ile Lys Ser Phe Ile Lys Lys Asn
                930                 935                 940

Gln Thr Glu Phe Ser Ile Ile Arg Ala Gly Gly Phe Ser Thr Thr Lys
945                 950                 955                 960

Phe Ile Val Gly Met Ser Val Phe Ala Gly Ile Val Ala Ile Val Ser
                965                 970                 975

Ser Phe Leu Gly Val Leu Phe Ala Phe Leu Leu Glu Gly Gln Val Lys
                980                 985                 990

Gly Ile Ile Asn Arg Tyr Trp Phe Ile Ala Leu Pro Glu Asn Ser Phe
                995                 1000                1005

Asn Trp Leu Ser Phe Phe Gly Ser Phe Phe Ile Thr Phe Phe Val
        1010                1015                1020

Phe Glu Phe Ile Ser Trp Ile Ala Phe Lys Gln Leu Phe Ser Lys
        1025                1030                1035

Pro Val Asn Val Leu Ile Asp Gln Gly Asn Glu Thr Lys Phe Ser
        1040                1045                1050

Val Leu Leu His Leu Leu Lys His Lys Ser His Thr Met Ser Pro
        1055                1060                1065

Leu Thr Lys Phe Arg Val Ser Leu Ile Val Ser Arg Phe Ser Arg
        1070                1075                1080

Leu Phe Thr Tyr Val Gly Leu Ser Ser Val Ala Leu Leu Leu Ile
        1085                1090                1095

Gly Ile Ala Gly Thr Ile Pro Gln Lys Phe Ser Ala Ala Gln Thr
        1100                1105                1110
```

-continued

```
Ser Thr Ser Leu Asn Arg Asn Phe Asn Tyr Lys Leu Asn Leu Gln
1115                1120                1125

Thr Pro Thr Glu Gln Ser Gly Trp Tyr Ala Ile Gln Pro Tyr Ser
1130                1135                1140

His Phe Gly Val Thr Asp Asn Asn Gly Ile Lys Thr Leu Tyr
1145                1150                1155

Asn Glu Ser Val Gln Ala Asn Ser Gln Asn Glu His Pro Tyr Lys
1160                1165                1170

Pro Ser Asn Leu Lys Leu Lys Asn Arg Gln Asp Gln Pro Ile Lys
1175                1180                1185

Ala Ala Asp Gly Thr Glu Leu Glu Leu Gly Asn Leu Leu Leu Pro
1190                1195                1200

Ser Tyr Gly Gly Ala Gln Gln Leu Asn Thr Asp Glu Asn Phe Phe
1205                1210                1215

Arg His Ala Ser Leu Ser Lys Trp Ile Ile Asp Phe Pro Ile Arg
1220                1225                1230

Val Gly Gly Ser Asn Ile Asn Pro Trp Glu Ile Val Glu Lys Ser
1235                1240                1245

Ile Pro Lys Gln Ile Thr Gln Leu Leu Ser Ala Ser Ser Asp Gln
1250                1255                1260

Phe Leu Ile Ser Val Leu Thr Asp Asp Phe Phe Asn Asn Leu Asn
1265                1270                1275

Ala Asn Gly Phe Leu Ile Arg Asn Pro Arg Thr Asn Gln Ile Gln
1280                1285                1290

Leu Asp Ala Ser Arg Val Leu Thr Thr Ile Asp Val Phe Asn Pro
1295                1300                1305

Gly Gly Val Lys Phe Asn Asp Ser Phe Leu Ser Phe Met Leu Lys
1310                1315                1320

Val Tyr Gly Asp Phe Glu Leu Ala Lys Gln Asp Ser Lys Leu Asn
1325                1330                1335

Phe Gly Ile Val Pro Val Asp Pro Ala Ile Glu Glu Thr Tyr Thr
1340                1345                1350

Tyr Val Glu Gly Pro Phe Gly Phe Gln Glu Asp Asn Leu Asp Glu
1355                1360                1365

Asn Ser Pro Tyr Thr Leu Thr Gly Ile Asn Pro Glu Ser Ser Phe
1370                1375                1380

Val Asn Leu Ile Asp Gly Ser Gly Asn Ser Leu Arg Asn Leu Ile
1385                1390                1395

Ser Ser Asp Gln Glu Met Asn Val Ile Val Asn Ala Gly Phe Gln
1400                1405                1410

Tyr Ala Asn Asn Ile Asn Ile Gly Asp Tyr Val Tyr Ile Lys Pro
1415                1420                1425

Lys Asn Thr Ala Thr Arg Tyr Ser Glu Lys Phe Leu Lys Ala Pro
1430                1435                1440

Leu Asn Asn Ser Thr Val Ala Phe Lys Val Val Gly Val Ser Thr
1445                1450                1455

Asp Ala Phe Gly Gln Glu Leu Tyr Ile Asn Gln His Ile Ala Asn
1460                1465                1470

Asn Leu Leu Lys Leu Ser Gly Asn Gln Gly Arg Gly Ile Ile Arg
1475                1480                1485

Asp Val Ile Lys Lys Thr Asn Gly Gln Ser Gln Ser Ser Asp Glu
1490                1495                1500
```

Tyr Glu Ile Asp Tyr Val Lys Pro Asn Gly Tyr Val Pro Phe Asn
    1505                1510                1515

Gly Val Phe Ser Lys Glu Leu Lys Pro Ser Leu Leu Asn Lys Ala
    1520                1525                1530

Leu Val Leu Asn Ser Ile Ile Gly Val Trp Gly Asn Phe Thr Asp
    1535                1540                1545

Phe Gly Asn Asn Phe Gln Asn Leu Val Arg Asn Lys Leu Asp Lys
    1550                1555                1560

Val Ile Thr Ser Ile Leu Pro Thr Asp Pro Glu Ile Ile Asn Lys
    1565                1570                1575

Leu Ala Gln Glu Lys Gln Ile Ile Asn Thr Thr Ser Met Asn Tyr
    1580                1585                1590

Glu Ser Leu Arg Lys Glu Leu Val Asn Lys Tyr Lys Thr Glu Trp
    1595                1600                1605

Asn Ser Val Asn Leu Leu Ser Gln Asn Ala Ser Ser Ile Phe Gly
    1610                1615                1620

Asn Asn Ile Ile Ala Pro Val Leu Asn Ile Asp Ala Ala Gly Thr
    1625                1630                1635

Ser Ala Gln Ile Ile Arg Asn Asn Ala Glu Val Leu Phe Asn Thr
    1640                1645                1650

Val Asn Gln Val Asp Ala Phe Leu Leu Gly Thr Ile Ile Pro Phe
    1655                1660                1665

Ile Phe Ile Thr Cys Val Val Leu Gly Ile Ser Met Leu Glu Glu
    1670                1675                1680

Met Lys Arg Ile Phe Ile Ser Leu Lys Ala Ile Gly Tyr Arg Asp
    1685                1690                1695

Val Gln Asn Leu Ile Ser Leu Thr Phe Phe Ile Pro Ala Phe
    1700                1705                1710

Val Leu Ala Leu Leu Ile Ser Ile Gly Val Leu Ala Gly Val Leu
    1715                1720                1725

Ile Gly Ile Gln Ala Val Val Phe Asn Val Ala Gln Val Phe Leu
    1730                1735                1740

Thr Asn Val Phe Glu Phe Leu Pro Tyr Met Val Gly Ile Val Leu
    1745                1750                1755

Phe Gly Val Thr Ile Phe Val Ile Gly Ser Tyr Phe Trp Ile Lys
    1760                1765                1770

Leu Arg Ser Ala Glu Leu Lys Glu Gly Phe
    1775                1780

<210> SEQ ID NO 2
<211> LENGTH: 134
<212> TYPE: PRT
<213> ORGANISM: artificial sequence
<220> FEATURE:
<223> OTHER INFORMATION: synthetic polypeptide

<400> SEQUENCE: 2

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
            20                  25                  30

Gln Leu Thr Val Trp Gly Ile Lys Gln Leu Gln Ala Arg Ile Leu Ala
        35                  40                  45

Val Glu Arg Tyr Leu Lys Asp Gln Gln Leu Leu Gly Ile Trp Gly Cys
    50                  55                  60

```
Ser Gly Lys Leu Ile Cys Thr Thr Ala Val Pro Trp Asn Ala Ser Trp
 65                  70                  75                  80

Ser Asn Lys Ser Leu Glu Gln Ile Trp Asn Asn Met Thr Trp Met Glu
                 85                  90                  95

Trp Asp Arg Glu Ile Asn Asn Tyr Thr Ser Leu Ile His Ser Leu Ile
            100                 105                 110

Glu Glu Ser Gln Asn Gln Gln Glu Lys Asn Glu Gln Glu Leu Leu Glu
        115                 120                 125

Leu Asp Lys Trp Ala Ser
    130

<210> SEQ ID NO 3
<211> LENGTH: 36
<212> TYPE: PRT
<213> ORGANISM: artificial sequence
<220> FEATURE:
<223> OTHER INFORMATION: synthetic polypeptide

<400> SEQUENCE: 3

Leu Val Gly Leu Arg Ile Val Phe Ala Val Leu Ser Ile Val Asn Arg
1               5                   10                  15

Val Arg Gln Gly Tyr Ser Pro Leu Ser Phe Gln Thr His Leu Pro Thr
            20                  25                  30

Pro Arg Gly Pro
        35

<210> SEQ ID NO 4
<211> LENGTH: 445
<212> TYPE: PRT
<213> ORGANISM: artificial sequence
<220> FEATURE:
<223> OTHER INFORMATION: synthetic polypeptide

<400> SEQUENCE: 4

Met Val Arg Asn Asn Asn Leu Ser Phe Gln Pro Ser Ser Asn Asn Leu
1               5                   10                  15

Gln Leu Val Gln Asn Gln Asn Ser Gln Ala Ser Asn Gly Ile Ala Asp
            20                  25                  30

Pro Asn Phe Ser Asn Val Gln Thr Ala Tyr Asn Lys Ile His Gln Ser
        35                  40                  45

Asn Asn Thr Pro Glu Lys Thr Leu Asp Ala Val Tyr Ala Ala Val Leu
 50                 55                  60

Asp Gln Trp Arg Ser Ile Phe Gln Glu Asp Leu Val Lys Lys Thr Val
 65                 70                  75                  80

Asp Leu Leu Glu Lys Tyr Arg Asp His Phe Leu Lys Ala Thr Ala Phe
                85                  90                  95

Asn Asn Ile Asp Tyr Ser Lys Gln Asn Ile Ala Ile Ala Asn Asn Val
            100                 105                 110

Ser Ser Ala Glu Ser Ala Ser Phe Leu Val Ser Asn Lys Asp Glu Gln
        115                 120                 125

Arg Tyr Asn Asp Leu Ser Leu Ile Asp Gly Val Asp Leu Lys Ser Trp
    130                 135                 140

Leu Phe Lys Pro Glu Gln Asn Glu Ser Asn Pro Leu Asp Thr Ile Tyr
145                 150                 155                 160

Gly Gly Gln Asp Ala Asn Asn Gly Phe Leu Gln Lys Ile Asp Tyr Glu
                165                 170                 175

Phe Lys Pro Ser Thr Ser Ser Gly Gly Met Thr Ala Ser Leu Lys Asn
            180                 185                 190
```

Thr Gln Ala Leu Ser Pro Lys Ser Thr Lys Phe Pro Ile Tyr Pro Lys
        195                 200                 205

Leu Ala Asn Ile Ile Ala Gln Ala Gln Leu Pro Glu Ala Thr Asn Ile
    210                 215                 220

Pro Thr Thr Ala Leu Asp Ala Leu Lys Gln Trp Thr Asn Leu Asp Ala
225                 230                 235                 240

Asn Gly Phe Asn Asn Leu Lys Glu Glu Asp Lys Arg Lys Ala Ala Asn
                245                 250                 255

Asn Tyr Leu Ala Leu Leu Ser Tyr Phe Thr Pro Ala Phe Gln Asp Pro
            260                 265                 270

Asn Glu Leu Ile Glu Thr Asn Arg Gln Met Leu Glu Ile Pro Ile Thr
        275                 280                 285

Val Lys Asn Gly Val Asn Pro Leu Ile Leu Pro Thr Asp Gln Gln Asn
    290                 295                 300

Leu Val Val Gln Thr Pro Glu Ala His Gly Ala Val Ser Gln Gln
305                 310                 315                 320

Trp Leu Phe Arg His Asn Lys Glu Ile Leu Pro Gln Glu Gly Glu Tyr
                325                 330                 335

Ala Trp Lys Thr Ala Leu Gln Thr Pro Asn Asn Phe Pro Asn Trp Leu
            340                 345                 350

Asn Asp Leu Pro Asp Arg Tyr Lys Phe Ser Ile Asn Gly Leu Thr Phe
        355                 360                 365

Ala Ile Leu Gly Ile Gly Glu Ser Val Glu Thr Gly Tyr Pro Val Leu
    370                 375                 380

Ser Leu Gln Ser Pro Leu Pro Asn Thr Gln Asp Glu Ala Leu Ile Phe
385                 390                 395                 400

Val Asn Asp Gln Ala Tyr Arg Ser Ile Leu Phe Ala Val Pro Ala Ala
                405                 410                 415

Asn Gln Glu Asn Tyr Tyr Ala Phe Lys Ser Thr Asp Leu Lys Gln His
            420                 425                 430

Thr Asp Gln Asp Pro Val Gln Phe Ile Ala Asn Arg Leu
        435                 440                 445

<210> SEQ ID NO 5
<211> LENGTH: 1338
<212> TYPE: DNA
<213> ORGANISM: artificial sequence
<220> FEATURE:
<223> OTHER INFORMATION: synthetic polynucleotide

<400> SEQUENCE: 5
atggtgcgca ataataatct gagctttcag ccgagcagca ataatctgca gctggtgcag    60
aatcagaata gccaggcaag caatggtatt gcagatccga attttagcaa tgttcagacc   120
gcctataata aaattcatca gagcaataat acaccggaaa aaccctgga tgcagtttat    180 gcagcagttc tggatcagtg gcgtagcatt tttcaggaag atctggttaa aaaaaccgtg   240
gatctgctgg aaaaatatcg cgatcatttt ctgaaagcca ccgcctttaa taatattgat   300
tatagcaaac agaatattgc cattgccaat aatgttagca gcgcagaaag cgcaagcttt   360
ctggtgagca taaagatga acagcgctat aatgatctga gctgattga tggtgttgat   420 ctgaaaagct ggctgtttaa ccggaacag aatgaaagca tccgctgga taccatttat   480 ggtggtcagg atgccaataa tggctttctg cagaaaattg attatgaatt taaaccgagc   540
accagcagcg gtggtatgac cgcaagcctg aaaaatacc aggcactgag cccgaaaagc   600

| | |
|---|---|
| accaaatttc cgatttatcc gaaactggcc aatattattg cacaggcaca gctgccggaa | 660 |
| gcaaccaata ttccgaccac cgcactggat gcactgaaac agtggaccaa tctggatgcc | 720 |
| aatggcttta ataatctgaa agaagaagat aaacgcaaag cagccaataa ttatctggca | 780 |
| ctgctgagct attttacacc ggcatttcag gatccgaatg aactgattga aaccaatcgt | 840 |
| cagatgctgg aaattccgat taccgtgaaa aatggtgtga atccgctgat cctgccgacc | 900 |
| gatcagcaga atctggttgt tcagacaccg gaagcacatg gtgcagttgt tagccagcag | 960 |
| tggctgtttc gtcataataa agaaattctg ccgcaggaag gtgaatatgc atggaaaacc | 1020 |
| gcactgcaga ccccgaataa ttttccgaat tggctgaatg atctgccgga tcgctataaa | 1080 |
| tttagcatta atggcctgac ctttgcaatt ctgggtattg gtgaaagcgt tgaaaccggt | 1140 |
| tatccggttc tgagcctgca gtctccgctg ccgaatacc aggatgaagc cctgattttt | 1200 |
| gttaatgatc aggcctatcg cagcattctg tttgcagttc cggcagcaaa tcaggaaaat | 1260 |
| tattacgcct ttaaaagcac cgatctgaaa cagcataccg atcaggatcc ggttcagttt | 1320 |
| attgcaaatc gcctgtaa | 1338 |

<210> SEQ ID NO 6
<211> LENGTH: 1359
<212> TYPE: DNA
<213> ORGANISM: artificial sequence
<220> FEATURE:
<223> OTHER INFORMATION: synthetic polynucleotide

<400> SEQUENCE: 6

| | |
|---|---|
| atggtgcgca ataataatct gagctttcag ccgagcagca ataatctgca gctggtgcag | 60 |
| aatcagaata gccaggcaag caatggtatt gcagatccga tttttagcaa tgttcagacc | 120 |
| gcctataata aaattcatca gagcaataat acaccggaaa aaaccctgga tgcagtttat | 180 |
| gcagcagttc tggatcagtg gcgtagcatt tttcaggaag atctggttaa aaaaaccgtg | 240 |
| gatctgctgg aaaatatcg cgatcatttt ctgaaagcca ccgcctttaa taatattgat | 300 |
| tatagcaaac agaatattgc cattgccaat aatgttagca gcgcagaaag cgcaagcttt | 360 |
| ctggtgagca taaagatga acagcgctat aatgatctga gctgattga tggtgttgat | 420 |
| ctgaaaagct ggctgtttaa accggaacag aatgaaagca tccgctgga taccatttat | 480 |
| ggtggtcagg atgccaataa tggctttctg cagaaaattg attatgaatt taaaccgagc | 540 |
| accagcagcg gtggtatgac cgcaagcctg aaaaatacc aggcactgag cccgaaaagc | 600 |
| accaaatttc gatttatcc gaaactggcc aatattattg cacaggcaca gctgccggaa | 660 |
| gcaaccaata ttccgaccac cgcactggat gcactgaaac agtggaccaa tctggatgcc | 720 |
| aatggcttta ataatctgaa agaagaagat aaacgcaaag cagccaataa ttatctggca | 780 |
| ctgctgagct attttacacc ggcatttcag gatccgaatg aactgattga aaccaatcgt | 840 |
| cagatgctgg aaattccgat taccgtgaaa aatggtgtga atccgctgat cctgccgacc | 900 |
| gatcagcaga atctggttgt tcagacaccg gaagcacatg gtgcagttgt tagccagcag | 960 |
| tggctgtttc gtcataataa agaaattctg ccgcaggaag gtgaatatgc atggaaaacc | 1020 |
| gcactgcaga ccccgaataa ttttccgaat tggctgaatg atctgccgga tcgctataaa | 1080 |
| tttagcatta atggcctgac ctttgcaatt ctgggtattg gtgaaagcgt tgaaaccggt | 1140 |
| tatccggttc tgagcctgca gtctccgctg ccgaatacc aggatgaagc cctgattttt | 1200 |
| gttaatgatc aggcctatcg cagcattctg tttgcagttc cggcagcaaa tcaggaaaat | 1260 |
| tattacgcct ttaaaagcac cgatctgaaa cagcataccg atcaggatcc ggttcagttt | 1320 | attgcaaatc gcctgcatca ccatcaccat cattaataa                               1359

<210> SEQ ID NO 7
<211> LENGTH: 451
<212> TYPE: PRT
<213> ORGANISM: artificial sequence
<220> FEATURE:
<223> OTHER INFORMATION: synthetic polypeptide

<400> SEQUENCE: 7

```
Met Val Arg Asn Asn Leu Ser Phe Gln Pro Ser Ser Asn Asn Leu
1               5                   10                  15

Gln Leu Val Gln Asn Gln Asn Ser Gln Ala Ser Asn Gly Ile Ala Asp
            20                  25                  30

Pro Asn Phe Ser Asn Val Gln Thr Ala Tyr Asn Lys Ile His Gln Ser
        35                  40                  45

Asn Asn Thr Pro Glu Lys Thr Leu Asp Ala Val Tyr Ala Val Leu
    50                  55                  60

Asp Gln Trp Arg Ser Ile Phe Gln Glu Asp Leu Val Lys Lys Thr Val
65                  70                  75                  80

Asp Leu Leu Glu Lys Tyr Arg Asp His Phe Leu Lys Ala Thr Ala Phe
                85                  90                  95

Asn Asn Ile Asp Tyr Ser Lys Gln Asn Ile Ala Ile Ala Asn Asn Val
            100                 105                 110

Ser Ser Ala Glu Ser Ala Ser Phe Leu Val Ser Asn Lys Asp Glu Gln
        115                 120                 125

Arg Tyr Asn Asp Leu Ser Leu Ile Asp Gly Val Asp Leu Lys Ser Trp
    130                 135                 140

Leu Phe Lys Pro Glu Gln Asn Glu Ser Asn Pro Leu Asp Thr Ile Tyr
145                 150                 155                 160

Gly Gly Gln Asp Ala Asn Asn Gly Phe Leu Gln Lys Ile Asp Tyr Glu
                165                 170                 175

Phe Lys Pro Ser Thr Ser Ser Gly Gly Met Thr Ala Ser Leu Lys Asn
            180                 185                 190

Thr Gln Ala Leu Ser Pro Lys Ser Thr Lys Phe Pro Ile Tyr Pro Lys
        195                 200                 205

Leu Ala Asn Ile Ile Ala Gln Ala Gln Leu Pro Glu Ala Thr Asn Ile
    210                 215                 220

Pro Thr Thr Ala Leu Asp Ala Leu Lys Gln Trp Thr Asn Leu Asp Ala
225                 230                 235                 240

Asn Gly Phe Asn Asn Leu Lys Glu Glu Asp Lys Arg Lys Ala Ala Asn
                245                 250                 255

Asn Tyr Leu Ala Leu Leu Ser Tyr Phe Thr Pro Ala Phe Gln Asp Pro
            260                 265                 270

Asn Glu Leu Ile Glu Thr Asn Arg Gln Met Leu Glu Ile Pro Ile Thr
        275                 280                 285

Val Lys Asn Gly Val Asn Pro Leu Ile Leu Pro Thr Asp Gln Gln Asn
    290                 295                 300

Leu Val Val Gln Thr Pro Glu Ala His Gly Ala Val Val Ser Gln Gln
305                 310                 315                 320

Trp Leu Phe Arg His Asn Lys Glu Ile Leu Pro Gln Glu Gly Glu Tyr
                325                 330                 335

Ala Trp Lys Thr Ala Leu Gln Thr Pro Asn Asn Phe Pro Asn Trp Leu
            340                 345                 350
```

Asn Asp Leu Pro Asp Arg Tyr Lys Phe Ser Ile Asn Gly Leu Thr Phe
            355                 360                 365

Ala Ile Leu Gly Ile Gly Glu Ser Val Glu Thr Gly Tyr Pro Val Leu
    370                 375                 380

Ser Leu Gln Ser Pro Leu Pro Asn Thr Gln Asp Glu Ala Leu Ile Phe
385                 390                 395                 400

Val Asn Asp Gln Ala Tyr Arg Ser Ile Leu Phe Ala Val Pro Ala Ala
                405                 410                 415

Asn Gln Glu Asn Tyr Tyr Ala Phe Lys Ser Thr Asp Leu Lys Gln His
                420                 425                 430

Thr Asp Gln Asp Pro Val Gln Phe Ile Ala Asn Arg Leu His His His
            435                 440                 445

His His His
        450

<210> SEQ ID NO 8
<211> LENGTH: 110
<212> TYPE: PRT
<213> ORGANISM: artificial sequence
<220> FEATURE:
<223> OTHER INFORMATION: synthetic polypeptide

<400> SEQUENCE: 8

Glu Val Gln Met Val Glu Ser Gly Gly Gly Leu Val Lys Pro Gly Gly
1               5                   10                  15

Ser Leu Lys Leu Ser Cys Ala Ala Ser Gly Phe Ala Phe Asn Lys Tyr
            20                  25                  30

Asp Met Ser Trp Val Arg Gln Thr Pro Ala Lys Arg Leu Glu Trp Val
        35                  40                  45

Ala Tyr Ile Ser Gly Gly Gly His Thr Tyr Tyr Arg Asp Thr Leu
    50                  55                  60

Lys Gly Arg Phe Thr Val Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Thr Arg His Gly Thr Ser Trp Asp Tyr Trp Gly Gln Gly Thr
            100                 105                 110

<210> SEQ ID NO 9
<211> LENGTH: 107
<212> TYPE: PRT
<213> ORGANISM: artificial sequence
<220> FEATURE:
<223> OTHER INFORMATION: synthetic polypeptide

<400> SEQUENCE: 9

Asp Ile Gln Met Asn Gln Ser Pro Ser Ser Leu Ser Ala Ser Leu Gly
1               5                   10                  15

Asp Thr Ile Ser Ile Thr Cys Arg Ala Ser Gln Asn Ile Asn Phe Trp
            20                  25                  30

Leu Ser Trp Tyr Gln Leu Lys Pro Gly Asn Ile Pro Lys Gln Leu Ile
        35                  40                  45

Tyr Lys Thr Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln Gly Gln Ser Tyr Pro Trp
                85                  90                  95

```
Thr Phe Gly Gly Gly Thr Lys Leu Glu Ile Lys
                100                 105
```

<210> SEQ ID NO 10
<211> LENGTH: 353
<212> TYPE: PRT
<213> ORGANISM: artificial sequence
<220> FEATURE:
<223> OTHER INFORMATION: synthetic polypeptide
<400> SEQUENCE: 10

```
Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Asn Lys Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
                165                 170                 175

Arg Asp Leu Cys Gly Cys Tyr Ser Val Ser Ser Val Leu Ser Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350
```

Tyr

<210> SEQ ID NO 11
<211> LENGTH: 106
<212> TYPE: PRT
<213> ORGANISM: artificial sequence
<220> FEATURE:
<223> OTHER INFORMATION: synthetic polypeptide

<400> SEQUENCE: 11

```
Ala Asp Ala Ala Pro Thr Val Ser Ile Phe Pro Pro Ser Ser Glu Gln
1               5                   10                  15
Leu Thr Ser Gly Gly Ala Ser Val Val Cys Phe Leu Asn Asn Phe Tyr
            20                  25                  30
Pro Lys Asp Ile Asn Val Lys Trp Lys Ile Asp Gly Ser Glu Arg Gln
        35                  40                  45
Asn Gly Val Leu Asn Ser Trp Thr Asp Gln Asp Ser Lys Asp Ser Thr
    50                  55                  60
Tyr Ser Met Ser Ser Thr Leu Thr Leu Thr Lys Asp Glu Tyr Glu Arg
65                  70                  75                  80
His Asn Ser Tyr Thr Cys Glu Ala Thr His Lys Thr Ser Thr Ser Pro
                85                  90                  95
Ile Val Lys Ser Phe Asn Arg Asn Glu Cys
            100                 105
```

<210> SEQ ID NO 12
<211> LENGTH: 415
<212> TYPE: DNA
<213> ORGANISM: artificial sequence
<220> FEATURE:
<223> OTHER INFORMATION: synthetic polynucleotide

<400> SEQUENCE: 12

```
actagaattc atgaactttg ggctcagctt ggttttcctt gtccttactt taaaaggtgt      60
gaagtgtgaa gtccagatgg tggagtctgg gggaggctta gtgaagcctg agggtccct     120
gaaactctcc tgtgcagcct ctggattcgc tttcaacaaa tatgacatgt cttgggttcg     180
ccagactccg gcgaagaggc tggagtgggt cgcatacatt agtggtggtg gtggtcatac     240
ttactatcga gacactttga agggccgctt caccgtctcc agagacaatg ccaagaacac     300
cctataccta caaatgaaca gtctgaagtc tgaagacaca gccatgtatt actgtacaag     360
acacggtact agctgggact actggggcca aggcaccgct ctcactgtct cctca         415
```

<210> SEQ ID NO 13
<211> LENGTH: 394
<212> TYPE: DNA
<213> ORGANISM: artificial sequence
<220> FEATURE:
<223> OTHER INFORMATION: synthetic polynucleotide

<400> SEQUENCE: 13

```
actatgtaca atgagtgtgc tcactcaggt cctggcgttg ctgctgttct gcttttagg      60
tgtgagatgt gacatccaga tgaaccagtc tccatccagt ctgtctgcat ccctcggaga     120
cacaatttcc atcacttgcc gtgccagtca gaacattaat ttttggttga gctggtacca     180
gctgaaacca ggaaatattc ctaaacaatt gatctataag acttccaact gcacacagg      240
cgtcccatca aggtttagtg gcagtggatc tggaacagat tcacattaa ccatcagcag     300
tctgcagcct gaagacattg ccacttacta ctgtctccag ggtcagagtt atccgtggac     360
```

```
gttcggtggg ggcaccaaac tggaaatcaa acgg                                       394
```

<210> SEQ ID NO 14
<211> LENGTH: 861
<212> TYPE: PRT
<213> ORGANISM: Human immunodeficiency virus

<400> SEQUENCE: 14

```
Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Gly Asn Ala Thr Asn Thr Asn Ser Ser Asn
    130                 135                 140

Thr Asn Ser Ser Ser Gly Glu Met Met Met Glu Lys Gly Glu Ile Lys
145                 150                 155                 160

Asn Cys Ser Phe Asn Ile Ser Thr Ser Ile Arg Gly Lys Val Gln Lys
                165                 170                 175

Glu Tyr Ala Phe Phe Tyr Lys Leu Asp Ile Ile Pro Ile Asp Asn Asp
            180                 185                 190

Thr Thr Ser Tyr Thr Leu Thr Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asn Lys Thr Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Ala Asn Phe Thr Asp Asn Ala Lys Thr
        275                 280                 285

Ile Ile Val Gln Leu Asn Gln Ser Val Glu Ile Asn Cys Thr Arg Pro
    290                 295                 300

Asn Asn Asn Thr Arg Lys Ser Ile Arg Ile Gln Arg Gly Pro Gly Arg
305                 310                 315                 320

Ala Phe Val Thr Ile Gly Lys Ile Gly Asn Met Arg Gln Ala His Cys
                325                 330                 335

Asn Ile Ser Arg Ala Lys Trp Asn Ala Thr Leu Lys Gln Ile Ala Ser
            340                 345                 350

Lys Leu Arg Glu Gln Phe Gly Asn Asn Lys Thr Ile Ile Phe Lys Gln
        355                 360                 365
```

```
Ser Ser Gly Gly Asp Pro Glu Ile Val Thr His Ser Phe Asn Cys Gly
    370                 375                 380

Gly Glu Phe Phe Tyr Cys Asn Ser Thr Gln Leu Phe Asn Ser Thr Trp
385                 390                 395                 400

Phe Asn Ser Thr Trp Ser Thr Glu Gly Ser Asn Asn Thr Glu Gly Ser
                405                 410                 415

Asp Thr Ile Thr Leu Pro Cys Arg Ile Lys Gln Phe Ile Asn Met Trp
            420                 425                 430

Gln Glu Val Gly Lys Ala Met Tyr Ala Pro Pro Ile Ser Gly Gln Ile
        435                 440                 445

Arg Cys Ser Ser Asn Ile Thr Gly Leu Leu Leu Thr Arg Asp Gly Gly
    450                 455                 460

Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Arg Glu Lys Arg Ala Val Gly Ile Gly Ala Leu Phe Leu Gly Phe Leu
        515                 520                 525

Gly Ala Ala Gly Ser Thr Met Gly Ala Arg Ser Met Thr Leu Thr Val
    530                 535                 540

Gln Ala Arg Gln Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Ile Leu Ala Val Glu Arg Tyr Leu
            580                 585                 590

Lys Asp Gln Gln Leu Leu Gly Ile Trp Gly Cys Ser Gly Lys Leu Ile
        595                 600                 605

Cys Thr Thr Ala Val Pro Trp Asn Ala Ser Trp Ser Asn Lys Ser Leu
    610                 615                 620

Glu Gln Ile Trp Asn Asn Met Thr Trp Met Glu Trp Asp Arg Glu Ile
625                 630                 635                 640

Asn Asn Tyr Thr Ser Leu Ile His Ser Leu Ile Glu Glu Ser Gln Asn
                645                 650                 655

Gln Gln Glu Lys Asn Glu Gln Glu Leu Leu Glu Leu Asp Lys Trp Ala
            660                 665                 670

Ser Leu Trp Asn Trp Phe Asn Ile Thr Asn Trp Leu Trp Tyr Ile Lys
        675                 680                 685

Ile Phe Ile Met Ile Val Gly Gly Leu Val Gly Leu Arg Ile Val Phe
    690                 695                 700

Ala Val Leu Ser Ile Val Asn Arg Val Arg Gln Gly Tyr Ser Pro Leu
705                 710                 715                 720

Ser Phe Gln Thr His Leu Pro Thr Pro Arg Gly Pro Asp Arg Pro Glu
                725                 730                 735

Gly Ile Glu Glu Glu Gly Gly Glu Arg Asp Arg Asp Arg Ser Ile Arg
            740                 745                 750

Leu Val Asn Gly Ser Leu Ala Leu Ile Trp Asp Asp Leu Arg Ser Leu
        755                 760                 765

Cys Leu Phe Ser Tyr His Arg Leu Arg Asp Leu Leu Leu Ile Val Thr
    770                 775                 780
```

```
Arg Ile Val Glu Leu Leu Gly Arg Arg Gly Trp Glu Ala Leu Lys Tyr
785                 790                 795                 800

Trp Trp Asn Leu Leu Gln Tyr Trp Ser Gln Glu Leu Lys Asn Ser Ala
            805                 810                 815

Val Ser Leu Leu Asn Ala Thr Ala Ile Ala Val Ala Glu Gly Thr Asp
            820                 825                 830

Arg Val Ile Glu Val Val Gln Gly Ala Cys Arg Ala Ile Arg His Ile
            835                 840                 845

Pro Arg Arg Ile Arg Gln Gly Leu Glu Arg Ile Leu Leu
    850                 855                 860

<210> SEQ ID NO 15
<211> LENGTH: 11
<212> TYPE: PRT
<213> ORGANISM: artificial sequence
<220> FEATURE:
<223> OTHER INFORMATION: synthetic peptide

<400> SEQUENCE: 15

Gly Gly Gly Gly Ser His His His His His
1               5                   10

<210> SEQ ID NO 16
<211> LENGTH: 144
<212> TYPE: PRT
<213> ORGANISM: artificial sequence
<220> FEATURE:
<223> OTHER INFORMATION: synthetic polynucleotide

<400> SEQUENCE: 16

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln Gln His Leu Leu
            20                  25                  30

Gln Leu Thr Val Trp Gly Ile Lys Gln Leu Gln Ala Arg Ile Leu Ala
        35                  40                  45

Val Glu Arg Tyr Leu Lys Asp Gln Gln Leu Leu Gly Ile Trp Gly Cys
    50                  55                  60

Ser Gly Lys Leu Ile Cys Thr Thr Ala Val Pro Trp Asn Ala Ser Trp
65                  70                  75                  80

Ser Asn Lys Ser Leu Glu Gln Ile Trp Asn Asn Met Thr Trp Met Glu
                85                  90                  95

Trp Asp Arg Glu Ile Asn Asn Tyr Thr Ser Leu Ile His Ser Leu Ile
            100                 105                 110

Glu Glu Ser Gln Asn Gln Gln Glu Lys Asn Glu Gln Glu Leu Leu Glu
        115                 120                 125

Leu Asp Lys Trp Ala Ser Gly Gly Gly Ser His His His His
    130                 135                 140

<210> SEQ ID NO 17
<211> LENGTH: 112
<212> TYPE: PRT
<213> ORGANISM: artificial sequence
<220> FEATURE:
<223> OTHER INFORMATION: synthetic polypeptide

<400> SEQUENCE: 17

Gln Val Gln Leu Val Gln Ser Gly Gly Gln Met Lys Lys Pro Gly Glu
1               5                   10                  15

Ser Met Arg Ile Ser Cys Arg Ala Ser Gly Tyr Glu Phe Ile Asp Cys
```

```
                    20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Pro Leu
 50                  55                  60

Gln Gly Arg Val Thr Met Thr Arg Asp Val Tyr Ser Asp Thr Ala Phe
 65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
                100                 105                 110
```

<210> SEQ ID NO 18
<211> LENGTH: 98
<212> TYPE: PRT
<213> ORGANISM: artificial sequence
<220> FEATURE:
<223> OTHER INFORMATION: synthetic polypeptide

<400> SEQUENCE: 18

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg
```

<210> SEQ ID NO 19
<211> LENGTH: 116
<212> TYPE: PRT
<213> ORGANISM: artificial sequence
<220> FEATURE:
<223> OTHER INFORMATION: synthetic polypeptide

<400> SEQUENCE: 19

```
Glu Val Gln Met Val Glu Ser Gly Gly Gly Leu Val Lys Pro Gly Gly
 1               5                  10                  15

Ser Leu Lys Leu Ser Cys Ala Ala Ser Gly Phe Ala Phe Asn Lys Tyr
                20                  25                  30

Asp Met Ser Trp Val Arg Gln Thr Pro Ala Lys Arg Leu Glu Trp Val
            35                  40                  45

Ala Tyr Ile Ser Gly Gly Gly His Thr Tyr Tyr Arg Asp Thr Leu
 50                  55                  60

Lys Gly Arg Phe Thr Val Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                85                  90                  95

Thr Arg His Gly Thr Ser Trp Asp Tyr Trp Gly Gln Gly Thr Ala Leu
                100                 105                 110

Thr Val Ser Ser
```

```
<210> SEQ ID NO 20
<211> LENGTH: 121
<212> TYPE: PRT
<213> ORGANISM: artificial sequence
<220> FEATURE:
<223> OTHER INFORMATION: synthetic polypeptide

<400> SEQUENCE: 20

Glu Val Lys Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asp Tyr
             20                  25                  30

Tyr Met Tyr Trp Val Arg Gln Thr Pro Glu Lys Arg Leu Glu Trp Val
         35                  40                  45

Ala Tyr Ile Ser Asn Gly Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
             85                  90                  95

Ala Arg Gly Lys Asn Cys Asp Tyr Asn Trp Asp Phe Glu His Trp Gly
            100                 105                 110

Arg Gly Thr Pro Val Ile Val Ser Ser
            115                 120
```